US010888636B2

(12) United States Patent
Angle et al.

(10) Patent No.: US 10,888,636 B2
(45) Date of Patent: Jan. 12, 2021

(54) CURABLE CALCIUM PHOSPHATE COMPOSITIONS FOR USE WITH POROUS STRUCTURES AND METHODS OF USING THE SAME

(71) Applicant: ZIMMER KNEE CREATIONS, INC., Exton, PA (US)

(72) Inventors: Siddhesh Angle, Allston, MA (US); Michael Strunk, Exton, PA (US); Tak Lung Chang, Exton, PA (US); Bradford J. Coale, Chester, NJ (US); Greg Stebbins, Hoboken, NJ (US); Imants Liepins, Asbury, NJ (US)

(73) Assignee: ZIMMER KNEE CREATIONS, INC., Exton, PA (US)

( * ) Notice: Subject to any disclaimer, the term of this patent is extended or adjusted under 35 U.S.C. 154(b) by 103 days.

(21) Appl. No.: 15/288,149

(22) Filed: Oct. 7, 2016

(65) Prior Publication Data

US 2017/0100507 A1    Apr. 13, 2017

Related U.S. Application Data

(60) Provisional application No. 62/238,776, filed on Oct. 8, 2015.

(51) Int. Cl.
| *A61L 27/20* | (2006.01) |
| *A61L 27/46* | (2006.01) |
| *A61L 27/56* | (2006.01) |
| *A61L 27/42* | (2006.01) |
| *A61L 27/12* | (2006.01) |
| *A61L 27/30* | (2006.01) |
| *A61L 27/36* | (2006.01) |

(52) U.S. Cl.
CPC .............. *A61L 27/20* (2013.01); *A61L 27/12* (2013.01); *A61L 27/306* (2013.01); *A61L 27/365* (2013.01); *A61L 27/3608* (2013.01); *A61L 27/3616* (2013.01); *A61L 27/422* (2013.01); *A61L 27/427* (2013.01); *A61L 27/46* (2013.01); *A61L 27/56* (2013.01); *A61L 2400/06* (2013.01); *A61L 2400/08* (2013.01); *A61L 2430/02* (2013.01); *A61L 2430/24* (2013.01)

(58) Field of Classification Search
None
See application file for complete search history.

(56) References Cited

U.S. PATENT DOCUMENTS

| 5,282,861 A | * | 2/1994 | Kaplan | A61F 2/28 623/23.51 |
| 2006/0088601 A1 | | 4/2006 | Overby et al. | |
| 2007/0128245 A1 | | 6/2007 | Rosenberg et al. | |
| 2008/0028992 A1 | * | 2/2008 | Lee | A61L 24/0015 106/690 |
| 2010/0185299 A1 | * | 7/2010 | Nies | A61F 2/28 623/23.53 |
| 2013/0178947 A1 | * | 7/2013 | Monaghan | A61L 27/56 623/23.55 |

FOREIGN PATENT DOCUMENTS

| CA | 2861590 A1 | 7/2013 |
| CA | 2933617 A1 | 6/2015 |
| CN | 102387822 | 3/2012 |
| CN | 103313733 | 9/2013 |
| CN | 108367095 A | 8/2018 |
| EP | 0560279 | 6/2000 |
| WO | WO-2005117919 A2 | 12/2005 |
| WO | WO-2009097412 A2 | 8/2009 |
| WO | WO-2012109748 A1 | 8/2012 |
| WO | WO-2013106323 A1 | 7/2013 |
| WO | WO-2017062737 A1 | 4/2017 |

OTHER PUBLICATIONS

Trabecular Metal™ Technology_ Zimmer Biomet, accessed from http://www.zimmer-biomet.com/medical-professionals/common/our-science/trabecular-metal-technology.html on Oct. 23, 2017.*
Yang, H., et al., Materials Letters 100: 152-155 (2013). (Year: 2013).*
"International Application Serial No. PCT/US2016/055940, International Search Report dated Jan. 19, 2017", 4 pgs.
"International Application Serial No. PCT/US2016/055940, Written Opinion dated Jan. 19, 2017", 7 pgs.
"International Application Serial No. PCT/US2016/055940, International Preliminary Report on Patentability dated Apr. 19, 2018", 9 pgs.
"Australian Application Serial No. 2016335711, First Examiner's Report dated Jul. 20, 2018", 3 pgs.
"European Application Serial No. 16784677.3, Response filed Dec. 11, 2018 to Communication pursuant to Rules 161(2) and 162 EPC dated Jun. 1, 2018", 19 pgs.
"Canadian Application Serial No. 3,000,872, Examiner's Rule 30(2) Requisition dated Jun. 12, 2019", 4 pgs.
"Canadian Application Serial No. 3,000,872, Response filed Nov. 19, 2019 to Examiner's Rule 30(2) Requisition dated Jun. 12, 2019", 23 pages.

(Continued)

*Primary Examiner* — David J Blanchard
*Assistant Examiner* — Daniel F. Coughlin
(74) *Attorney, Agent, or Firm* — Schwegman Lundberg & Woessner, P.A.

(57) ABSTRACT

Various embodiments disclosed relate to curable calcium phosphate compositions for use with porous structures and methods of using the same. In various embodiments, the present invention provides a curable calcium phosphate composition or a cured product thereof, with the curable calcium phosphate composition including calcium phosphate and a perfusion modifier. In various embodiments, the present invention provides an apparatus comprising a porous structure at least partially in contact with the curable calcium phosphate composition or a cured product thereof. The porous structure can include a porous substrate including a plurality of ligaments that define pores of the porous substrate, and a biocompatible metal coating on the plurality of ligaments of the porous substrate.

17 Claims, 6 Drawing Sheets

(56) References Cited

OTHER PUBLICATIONS

"European Application Serial No. 16784677.3, Communication Pursuant to Article 94(3) EPC dated Jan. 17, 2020", 7 pages.
"European Application Serial No. 16784677.3, Response filed May 22, 2020 to Communication Pursuant to Article 94(3) EPC dated Jan. 17, 2020", 17 pages.
"Chinese Application Serial No. 201680071834.9, Office Action dated Aug. 26, 2020", with English translation, 20 pages.
Yang, Hailin, "Structural preparation and biocompatibility evaluation of highly porous Tantalum scaffolds", Materials Letters, (Jan. 23, 2013), pp. 152-155.

* cited by examiner

CURABLE CALCIUM PHOSPHATE COMPOSITIONS FOR USE WITH POROUS STRUCTURES AND METHODS OF USING THE SAME

CLAIM OF PRIORITY

This application claims the benefit of U.S. Provisional Patent Application Ser. No. 62/238,776, filed on Oct. 8, 2015, the benefit of priority of which is claimed hereby, and which is incorporated by reference herein in its entirety.

BACKGROUND

Healthy trabecular or cancellous human bone has interconnected pores in the range of 100-600 microns in diameter and has a compressive strength of nominally 0.5-10 MPa. The structure of trabecular bone has an important role in the tolerance of skeletal tissue to mechanical stresses. Typical methods for implantation of orthopedic devices that mimic the biomechanical properties of trabecular bone leave regions of the remaining host bone not contacted to or interfaced with the orthopedic device, decreasing the security and rigidity with which the implant is seated in the remaining host bone, slowing healing and osteo-incorporation into the implant, and increasing the likelihood of revision surgery.

SUMMARY OF THE INVENTION

In various embodiments, the present invention provides a curable calcium phosphate composition. The curable calcium phosphate composition includes calcium phosphate and a perfusion modifier. In some embodiments, the present invention provides a cured product of the curable calcium phosphate composition. In some embodiments, the present invention provides a method including using the curable calcium phosphate composition or a cured product thereof for treatment of a joint disorder or condition.

In various embodiments, the present invention provides an apparatus. The apparatus includes a porous structure at least partially in contact with a curable calcium phosphate composition or a cured product thereof, with the curable calcium phosphate composition including calcium phosphate and a perfusion modifier. In some embodiments, the present invention provides a method of making the apparatus. The method of making the apparatus can include placing the curable calcium phosphate composition at least partially in contact with the porous structure to form the apparatus. In some embodiments, the present invention provides a method including using the apparatus for treatment of a joint disorder or condition.

In some embodiments, the porous structure includes a porous substrate including a plurality of ligaments that define pores of the porous substrate. In some embodiments, the porous substrate can include reticulated vitreous carbon foam. The porous structure can also include a biocompatible metal coating on the plurality of ligaments of the porous substrate. In some embodiments, the biocompatible metal coating can include tantalum metal.

Various embodiments of the present invention provide certain advantages over other compositions, apparatuses, and methods of using the same, at least some of which are unexpected. For example, in various embodiments, the composition, apparatus, and method of using the same can provide increased contact between the host bone and an orthopedic implant. In some embodiments, by providing increased contact between the host bone and the implant, the composition, apparatus, and method of using the same can provide a more rigid and secure connection between the host bone and the implant (e.g., decreasing the chance of implant loosening). In some embodiments, by providing increased contact between the host bone and the implant, the composition, apparatus, and method of using the same can provide increased healing speed, increased speed of osteo-incorporation into the implant, and increased extent of osteo-incorporation into the implant. In some embodiments, by providing increased contact between the host bone and the implant, the composition, apparatus, and method of using the same can provide a decreased chance that revision surgery will be needed, or can increase the time span between implantation and revision surgery.

In various embodiments, the curable calcium phosphate composition can be a reactive precursor to a bone-remodelable solid (e.g., the cured product of the curable calcium phosphate composition). As used herein, "bone-remodelable" refers to a process including resorption of the material (e.g., removal) followed by ossification (e.g., new bone formation). In various embodiments, the cured product of the curable calcium phosphate composition can be more bone-remodelable than other compositions, such as other bone substitute materials, remodeling more quickly, more completely, or a combination thereof. In various embodiments (e.g., prior to hydration), the curable calcium phosphate composition can provide a stable intermediate for production of a reactive precursor to a bone-remodelable solid. In various embodiments, the stable intermediate can be more stable, can be stored for longer periods, or a combination thereof, as compared to other compositions for forming bone-remodelable solids. In various embodiments, the curable calcium phosphate composition can provide more controlled and predictable crystallization kinetics (e.g., to form the cured product of the composition) than other compositions. In various embodiments, the curable composition can provide reduced or no phase separation between reactive solids and carrier fluid during use. In various embodiments, the curable composition can provide reduced or no phase separation or premature crystallization of the cured product of the composition during use, as compared to other compositions that form bone-remodelable materials.

In various embodiments, the curable calcium phosphate composition can enhance the biomechanical properties and eventual integration of a porous structure into bone. In various embodiments, the curable calcium phosphate composition can be used in contact with a porous structure to increase integration of new bone with porous surfaces of the porous structure. In various embodiments, the cured product of the curable calcium phosphate composition can provide a bone-remodelable conductive scaffold for integration of new bone with the surface of the porous structure. In various embodiments, the cured product of the curable calcium phosphate composition can form an uninterrupted or less interrupted conductive interface with the surrounding host bone and augment the porous structure. In various embodiments, the curable calcium phosphate composition can have a flowability and viscosity that is suitable for injecting not only around a porous structure but also at least partially within the porous structure (e.g., perfused within). In various embodiments, the curable calcium phosphate composition can at least partially be used inside the porous structure, causing increased speed and extent of bone interdigitation within the porous structure during the recovery process.

In various embodiments, the method of using the curable calcium phosphate composition, the cured product thereof, or the method of using or forming the apparatus including the porous structure and the curable composition or a cured product thereof, can be compatible with minimally invasive surgical techniques. In various embodiments, the curable calcium phosphate composition can accelerate osseous integration, such as of the porous structure, such as via osteoconductivity of the cured product thereof. In various embodiments, the curable calcium phosphate composition can be conveniently injected with nominal digital (i.e., finger) pressure. In various embodiments, augmentation of implants with the curable calcium phosphate composition can enhance bone ingrowth and end-to-end fusion (e.g., with an ankle fusion implant).

BRIEF DESCRIPTION OF THE FIGURES

The drawings are not necessarily drawn to scale. The drawings illustrate generally, by way of example, but not by way of limitation, various embodiments discussed in the present document.

DETAILED DESCRIPTION OF THE INVENTION

Figure 1:
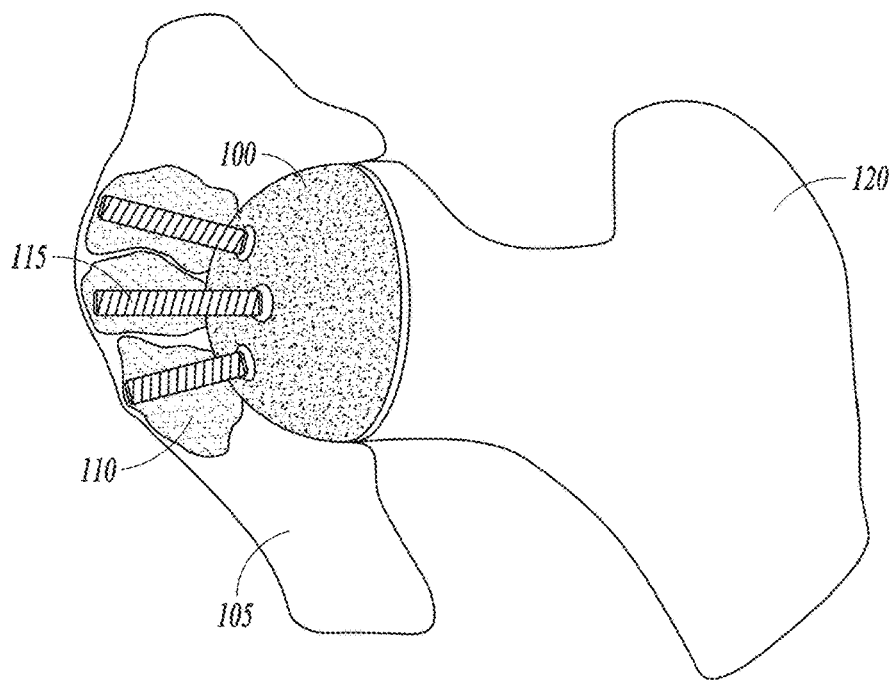
FIG. 1 illustrates an implanted apparatus including a curable calcium phosphate composition and a porous structure, in accordance with various embodiments.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

As used herein, the term "polymer" refers to a molecule having at least one repeating unit and can include copolymers.

In various embodiments, salts having a positively charged counterion can include any suitable positively charged counterion. For example, the counterion can be ammonium ($NH_4^+$), or an alkali metal such as sodium ($Na^+$), potassium ($K^+$), or lithium ($Li^+$). In some embodiments, the counterion can have a positive charge greater than +1, which can in some embodiments complex to multiple ionized groups, such as $Zn^{2+}$, $Al^{3+}$ or alkaline earth metals such as $Ca^{2+}$ or $Mg^{2+}$.

In various embodiments, salts having a negatively charged counterion can include any suitable negatively charged counterion. For example, the counterion can be a halide, such as fluoride, chloride, iodide, or bromide. In other examples, the counterion can be nitrate, hydrogen sulfate, dihydrogen phosphate, bicarbonate, nitrite, perchlorate, iodate, chlorate, bromate, chlorite, hypochlorite, hypobromite, cyanide, amide, cyanate, hydroxide, permanganate. The counterion can be a conjugate base of any carboxylic acid, such as acetate or formate. In some embodiments, a counterion can have a negative charge greater than −1, which can in some embodiments complex to multiple ionized groups, such as oxide, sulfide, nitride, arsenate, phosphate, arsenite, hydrogen phosphate, sulfate, thiosulfate, sulfite, carbonate, chromate, dichromate, peroxide, or oxalate.

The polymers described herein can terminate in any suitable way. In some embodiments, the polymers can terminate with an end group that is independently chosen from a suitable polymerization initiator, —H, —OH, a substituted or unsubstituted $(C_1-C_{20})$hydrocarbyl (e.g., $(C_1-C_{10})$alkyl or $(C_6-C_{20})$aryl) interrupted with 0, 1, 2, or 3 groups independently selected from —O—, substituted or unsubstituted —NH—, and —S—, a poly(substituted or unsubstituted $(C_1-C_{20})$hydrocarbyloxy), and a poly(substituted or unsubstituted $(C_1-C_{20})$hydrocarbylamino).

Curable Calcium Phosphate Composition, or Cured Product Thereof.

In various embodiments, the present invention provides a curable calcium phosphate composition. The curable calcium phosphate composition includes calcium phosphate and a perfusion modifier. The curable calcium phosphate composition, in an unhydrated state, can be in the form of a powder, such as a flowable powder. In a hydrated state, the curable calcium phosphate composition can be in the form of a flowable paste or putty having a consistency and viscosity that is suitable for perfusion into and around a porous structure, and that can be suitable for injection through a needle. In a hydrated state, the curable calcium phosphate composition can be moldable and cohesive when applied to an implant site in vivo. The curable calcium phosphate composition, in a hydrated state, can cure (e.g., harden) to form a cured product of the curable calcium phosphate composition. The curable calcium phosphate composition can be self-curable, such that in a hydrated state, the composition cures to form a solid material without using any curing accelerators and without exposing the curable composition to particular conditions for curing.

The cured product can have a different composition than the curable calcium phosphate composition (e.g., during curing, reaction products of the curable composition can form that are different than the components of the curable composition). The cured product of the calcium phosphate composition can approximate the chemical composition of natural bone. The cured product of the calcium phosphate composition can include calcium phosphate (e.g., any one or more materials that qualify as a calcium phosphate, and not necessarily the same one or more materials that were present in the curable composition). The cured product of the calcium phosphate composition can be suitable as a bone-substitute material, can be used to repair bone (e.g., damaged bone), can be bone-remodelable, and can be sufficiently strong and rigid to provide structural support to the surrounding regions of a host bone. The cured product of the calcium phosphate composition can be used as a delivery vehicle for biologically active materials (e.g., wherein the biologically active materials can be present in the curable composition, or can be added to the cured product after formation thereof). The cured product of the calcium phosphate composition can be formed outside a patient and then implanted, or the curable composition can be implanted in a patient and then allowed to cure in vivo.

The curable calcium phosphate composition can be in an unhydrated state (e.g., a powder) or a hydrated state (e.g., a paste). When the curable calcium phosphate is in a hydrated state, at least some aqueous fluid is present in the curable calcium phosphate composition, such as water or saline. The amount of fluid in the composition can be adjusted to provide a desired consistency of the hydrated curable calcium phosphate composition (e.g., more or less viscous). The aqueous fluid can be about 0.001 wt % to about 99.999 wt % of the composition, about 30 wt % to about 60 wt %, about 40 wt % to about 50 wt %, or about 0.001 wt % or less, or less than, equal to, or more than 0.01 wt %, 0.1, 1, 2, 3, 4, 5, 6, 8, 10, 12, 14, 16, 18, 20, 25, 30, 32, 34, 36, 38, 40, 41, 42, 43, 44, 45, 46, 47, 48, 49, 50, 52, 54, 56, 58, 60, 65, 70, 75, 80, 82, 84, 86, 88, 90, 91, 92, 93, 94, 95, 96, 97, 98, 99, 99.9, 99.99 wt %, or about 99.999 wt % or more. The aqueous fluid can include a physiologically acceptable fluid. The physiologically acceptable fluid can include or can be water, saline, phosphate buffer, biological fluid, or a combination thereof. The biological fluid can include or can be blood (e.g., whole blood, warm or cold blood, and stored or fresh blood; treated blood, such as blood diluted with at least one physiological solution, including but not limited to saline, nutrient, or anticoagulant solutions, or a combination thereof), a blood component (e.g., platelet concentrate (PC), apheresed platelets, platelet-rich plasma (PRP), platelet-poor plasma (PPP), platelet-free plasma, plasma, serum, fresh frozen plasma (FFP), components obtained from plasma, packed red cells (PRC), buffy coat (BC), or a combination thereof), a blood product (e.g., blood products derived from blood or derived from bone marrow), milk, urine, saliva, seminal fluid, vaginal fluid, synovial fluid, lymph fluid, amniotic fluid, the fluid within a yolk sac of an egg, chorion of an egg, allantois of an egg, sweat, tears, or a combination thereof.

The calcium phosphate can be any one or more minerals that include at least one calcium ion ($Ca^{2+}$) and a phosphate, such as an orthophosphate ($PO_4^{3-}$), metaphosphate ($PO_3^{1-}$), a pyrophosphate ($P_2O_7^{4-}$). The calcium phosphate can include a hydrogen or hydroxide ion. The calcium phosphate can include one calcium phosphate mineral or more than one calcium phosphate mineral. The calcium phosphate (e.g., the one or more calcium phosphate minerals) can form any suitable proportion of the curable calcium phosphate composition, such as about 0.001 wt % to about 99.999 wt % of the composition, about 40 wt % to about 99.999 wt %, about 40 wt % to about 70 wt %, or about 40 wt % to about 60 wt %, or about 0.001 wt % or less, or less than, equal to, or more than about 0.01 wt %, 0.1, 1, 2, 3, 4, 5, 6, 8, 10, 12, 14, 16, 18, 20, 25, 30, 32, 34, 36, 38, 40, 41, 42, 43, 44, 45, 46, 47, 48, 49, 50, 51, 52, 53, 54, 55, 56, 57, 58, 59, 60, 62, 64, 66, 68, 70, 75, 80, 82, 84, 86, 88, 90, 91, 92, 93, 94, 95, 96, 97, 98, 99, 99.9, 99.99 wt %, or about 99.999 wt % or more. The calcium phosphate can include amorphous calcium phosphate, poorly crystalline calcium phosphate, hydroxyapatite, carbonated apatite (e.g., calcium-deficient hydroxyapatite), monocalcium phosphate, calcium metaphosphate, heptacalcium phosphate, dicalcium phosphate dihydrate, tetracalcium phosphate, octacalcium phosphate, calcium pyrophosphate, tricalcium phosphate, or a combination thereof. As used herein and applied to a calcium phosphate, the term "amorphous" means a calcium phosphate having no or only short range crystallographic order, e.g., crystallographic order over less than 100 nm. The calcium phosphate can include amorphous calcium phosphate and a second calcium phosphate including poorly crystalline calcium phosphate, hydroxyapatite, carbonated apatite (e.g., calcium-deficient hydroxyapatite), monocalcium phosphate, calcium metaphosphate, heptacalcium phosphate, dicalcium phosphate dihydrate, tetracalcium phosphate, octacalcium phosphate, calcium pyrophosphate, tricalcium phosphate, or a combination thereof. The calcium phosphate can include or can be a combination of amorphous calcium phosphate and dicalcium phosphate dihydrate, wherein the mass ratio of the amorphous calcium phosphate to the dicalcium phosphate dihydrate can be about 99:1 or more, or less than, equal to, or more than 19:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:19, or about 1:99 or less.

The perfusion modifier can be any one or more perfusion modifier compounds that, when included in the curable calcium phosphate composition of the invention, improve the ability of the calcium phosphate composition to infiltrate the porous network of a porous structure (e.g., at least the parts of the porous network at and near the surface of the porous structure), such as a porous network similar to a trabecular network of cancellous bone. The perfusion modifier (e.g., the one or more perfusion modifier compounds) can be any suitable proportion of the curable calcium phosphate composition, such as about 0.001 wt % to about 50 wt % of the composition, about 0.001 wt % to about 20 wt %, about 0.5 wt % to about 10 wt %, or about 0.001 wt % or less, or less than, equal to, or more than about 0.01 wt %, 0.1, 0.5, 1, 1.5, 2, 2.5, 3, 3.5, 4, 4.5, 5, 6, 8, 10, 12, 14, 16, 18, 20, 25, 30, 35, 40, 45 wt %, or about 50 wt % or more of the composition. The perfusion modifier can include or can be one or more polymers. The perfusion modifier can include or can be a polysaccharide, a nucleic acid, a carbohydrate, a protein, a polypeptide, a poly(α-hydroxy acid), a poly(lactone), a poly(amino acid), a poly(anhydride), a poly(orthoester), a poly(anhydride-co-imide), a poly(orthocarbonate), a poly(α-hydroxy alkanoate), a poly(dioxanone), a poly(phosphoester), sodium alginate, alginic acid, arabic gum, guar gum, xantham gum, gelatin, chitin, chitosan, chitosan acetate, chitosan lactate, chondroitin sulfate, N,O-carboxymethyl chitosan, a dextran (e.g., α-cyclodextrin, β-cyclodextrin, γ-cyclodextrin, or sodium dextran sulfate), fibrin glue, glycerol, hyaluronic acid, sodium hyaluronate, a cellulose (e.g., methylcellulose, carboxymethylcellulose, hydroxypropylmethylcellulose, hydroxyethylcellulose, a salt thereof, or a combination thereof), a glucosamine, a proteoglycan, a starch (e.g., starch or a starch derivative such as hydroxyethyl starch), lactic acid, a poly (ethylene oxide-co-propylene oxide) (e.g., Pluronic® series), sodium glycerophosphate, collagen, glycogen, a keratin, silk, poly(L-lactide) (PLLA), poly(D,L-lactide) (PDLLA), polyglycolide (PGA), poly(lactide-co-glycolide) (PLGA), poly(L-lactide-co-D, L-lactide), poly(D,L-lactide-co-trimethylene carbonate), polyhydroxybutyrate (PHB), poly(ε-caprolactone), poly(δ-valerolactone), poly(γ-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly (vinyl alcohol), poly(vinylpyrrolidone), poly(ethyloxazoline), poly(ethylene oxide)-co-polypropylene oxide) block copolymers, poly(ethylene terephthalate)polyamide, copolymers thereof, or a combination thereof. In some embodiments, the perfusion modifier can be a cellulose or cellulose derivative, such as carboxymethylcellulose. The perfusion modifier can be a lyophilized perfusion modifier, wherein one or more compounds in the perfusion modifier are lyophilized. For example, the perfusion modifier can be a calcium carboxymethylcellulose sponge or fibers lyophilized from a dilute basic aqueous solution of a calcium salt and sodium carboxymethylcellulose. Calcium ions can be exchanged and sequestered as a carboxylate salt, available to precipitate in solution with phosphates, available to quench anticoagulants such as ACD-A, or available to initiate platelet activation and clotting. Thus, the curable composition can include a lyophilized perfusion modifier stabilized by sequestration of ionic elements and ligands.

In some embodiments, the curable calcium phosphate composition includes a biologically active modifier. In some embodiments, the curable calcium phosphate composition is free of biologically active modifiers. The curable calcium phosphate composition can include one biologically active modifier or multiple biologically active modifiers. The one or more biologically active modifiers can form any suitable proportion of the curable calcium phosphate composition, such as about 0.001 wt % to about 40 wt % of the composition, about 0.001 wt % to about 10 wt %, or about 0.001 wt % or less, or less than, equal to, or more than about 0.01 wt %, 0.1, 1, 2, 3, 4, 5, 6, 7, 8, 9, 10, 12, 14, 16, 18, 20, 22, 24, 26, 28, 30, 32, 34, 36, 38, or about 40 wt % or more of the composition. The biologically activate modifier can be at least one of an antibody, an antibiotic, a polynucleotide, a polypeptide, a protein (e.g., an osteogenic protein, such as BMP-2, BMP-3, BMP-3b, BMP-4, BMP-5, BMP-6, BMP-7, BMP-8, BMP-9, BMP-10, BMP-11, BMP-12, BMP-13, BMP-14, BMP-15, BMP-16, BMP-17, BMP-18, or a combination thereof), an anti-cancer modifier, a growth factor, a vaccine, or a combination thereof. Anti-cancer modifiers can include alkylating modifiers, platinum modifiers, antimetabolites, topoisomerase inhibitors, antitumor antibiotics, antimitotic modifiers, aromatase inhibitors, thymidylate synthase inhibitors, DNA antagonists, farnesyltransferase inhibitors, pump inhibitors, histone acetyltransferase inhibitors, metalloproteinase inhibitors, ribonucleoside reductase inhibitors, TNF alpha agonists, TNF alpha antagonists, endothelin A receptor antagonists, retinoic acid receptor agonists, immuno-modulators, hormonal modifiers, antihormonal modifiers, photodynamic modifiers, and tyrosine kinase inhibitors.

In various embodiments, the curable calcium phosphate composition includes a binder. In some embodiments, the curable calcium phosphate composition is free of binders. The curable calcium phosphate composition can include one binder or more than one binder. The one or more binders can form any suitable proportion of the curable calcium phosphate composition, such as about 0.001 wt % to about 20 wt % of the composition, about 0.001 wt % to about 5 wt %, or about 0.001 wt % or less, or less than, equal to, or more than about 0.01 wt %, 0.1, 1, 2, 3, 4, 5, 6, 7, 8, 9, 10, 12, 14, 16, 18 wt %, or about 20 wt % or more. The binder can be at least one of a) a polysaccharide, a nucleic acid, a carbohydrate, a protein, a polypeptide, a poly(α-hydroxy acids), a poly(lactone), a poly(amino acid), a poly(anhydride), a poly(orthoester), a poly(anhydride-co-imide), a poly(orthocarbonate), a poly(α-hydroxy alkanoate), a poly(dioxanone), a poly(phosphoester), poly(L-lactide) (PLLA), poly(D,L-lactide) (PDLLA), polyglycolide (PGA), poly(lactide-co-glycolide) (PLGA), poly(L-lactide-co-D, L-lactide), poly(D,L-lactide-co-trimethylene carbonate), polyhydroxybutyrate (PHB), poly(ε-caprolactone), poly(δ-valerolactone), poly(γ-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, a polyethylene, polymethylmethacrylate, a carbon fiber, poly(ethylene glycol), poly (ethylene oxide), poly(vinyl alcohol), poly(vinylpyrrolidone), poly(ethyloxazoline), a poly(ethylene oxide)-co-poly (propylene oxide) block copolymer, poly(ethylene terephthalate)polyamide, and copolymers thereof; b) a homo- or co-polymer having one or more monomers selected from the group consisting of acrolein potassium, (meth)acrylamides, (meth)acrylic acid and salts thereof, (meth)acrylates, acrylonitrile, ethylene, ethylene glycol, ethyleneimine, ethyleneoxide, styrene sulfonate, vinyl acetate, vinyl alcohol, vinyl chloride, and vinylpyrrolidone); c) a polyphenol complexing agent selected from a gallotannin, a ellagitannin, a taragallotannin, a caffetannin, a proanthocyanidin, catechin, epicatechin, chlorogenic acid, and arbutin; and d) an agent selected from alginic acid, arabic gum, guar gum, xanthan gum, gelatin, chitin, chitosan, chitosan acetate, chitosan lactate, chondroitin sulfate, N,O-carboxymethyl chitosan, a dextran (e.g., α-cyclodextrin, β-cyclodextrin, γ-cyclodextrin, or sodium dextran sulfate), fibrin glue, glycerol, hyaluronic acid, sodium hyaluronate, a cellulose (e.g., methylcellulose, carboxymethylcellulose, hydroxypropylmethylcellulose, hydroxyethyl cellulose, a salt thereof, or a combination thereof), a glucosamine, a proteoglycan, a starch, lactic acid, a poly(ethylene oxide-co-propylene oxide), sodium glycerophosphate, collagen, glycogen, a keratin, and silk.

In various embodiments, the curable calcium phosphate composition includes an effervescent agent. In some embodiments, the curable calcium phosphate composition is free of an effervescent agent. The curable calcium phosphate composition can include one effervescent agent or multiple effervescent agents. The one or more effervescent agents can form any suitable proportion of the curable calcium phosphate composition, such as about 0.001 wt % to about 40 wt % of the composition, or about 0.001 wt % or less, or less than, equal to, or more than about 0.01 wt %, 0.1, 1, 2, 3, 4, 5, 6, 8, 10, 12, 14, 16, 18, 20, 22, 24, 26, 28, 30, 32, 34, 36, 38, or about 40 wt % or more. In some embodiments, the effervescent agent includes a combination of at least two compounds. The effervescent agent can include a carbonate compound and a bicarbonate compound which can react to form $CO_2$ gas upon hydration (or soon thereafter) of said composition. The carbonate and bicarbonate compounds can have a molar ratio of about 1:1 to about 1:9, or about 1:1 or less, or less than, equal to, or more than about 1:2, 1:3, 1:4, 1:5, 1:6, 1:7, 1:8, or about 1:9 or more. The carbonate and bicarbonate compounds can have any suitable counterion (e.g., the compounds can be sodium carbonate and sodium bicarbonate). The formed CO2 gas can form pores in the hardened material, such as pores having a size of about 1 micron to about 1000 microns, or about 10 microns to about 100 microns. The porosity of a cured product of the curable composition not including any effervescent compound can be about 0. The porosity of a cured product of the curable composition that includes an effervescent compound can be about 5% to about 60%, or 5% or less, or less than, equal to, or more than about 10%, 15, 20, 25, 30, 35, 40, 45, 50, 55%, or about 60% or more. In some embodiments, the effervescent agent produces a substantially continuous matrix of interconnected pores in the cured product of the curable calcium phosphate composition.

In some embodiments, the curable calcium phosphate composition includes demineralized bone. The curable calcium phosphate composition can include any suitable proportion of demineralized bone, such as about 0.001 wt % to about 40 wt % of the composition, or about 0.001 wt % or less, or less than, equal to, or more than about 0.01 wt %, 0.1, 1, 2, 3, 4, 5, 6, 7, 8, 9, 10, 12, 14, 16, 18, 20, 22, 24, 26, 28, 30, 32, 34, 36, 38 wt %, or about 40 wt % or more. The demineralized bone can include or can be demineralized bone fibers.

In various embodiments, the present invention provides a use of the curable calcium phosphate composition or a cured product thereof for treatment of a joint disorder or condition. For example, the present invention can provide a method including using the calcium phosphate composition or cured product thereof as an orthopedic implant, such as using the calcium phosphate composition in combination with a porous structure as an orthopedic implant. The method can include implanting a cured product of the curable calcium phosphate composition alone or with a porous structure, or can include implanting the curable calcium phosphate composition (e.g., alone or with a porous structure) and allowing the curable composition to cure.

Apparatus Including a Porous Structure.

In various embodiments, the present invention provides an apparatus including a porous structure at least partially in contact with the curable calcium phosphate composition or a cured product thereof. Any suitable proportion of the porous structure can be contacted with the curable calcium phosphate composition. For example, about 0.001% to about 100% of the outer surface of the porous structure can be in contact with the curable calcium phosphate composition or a cured product thereof, or about 0.001% or less, or less than, equal to, or more than about 0.01%, 0.1, 1, 2, 3, 4, 5, 6, 7, 8, 9, 10, 12, 14, 16, 18, 20, 25, 30, 35, 40, 45, 50, 55, 60, 65, 70, 75, 80, 82, 84, 86, 88, 90, 91, 92, 93, 94, 95, 96, 97, 98, 99, 99.9, 99.99, or about 99.999% or more. In some embodiments, the inner volume (e.g., pore space) of the porous structure can include the curable calcium phosphate composition or a cured product thereof, wherein 0% or about 0.001% to about 100% of the outer surface of the porous structure is in contact with the curable calcium phosphate composition or a cured product thereof. Any suitable amount of the pore space of the porous structure can be filled with the curable calcium phosphate composition or a cured product thereof, such as 0%, or such as about 0.001% or less, or less than, equal to, or more than about 0.01%, 0.1, 1, 2, 3, 4, 5, 6, 7, 8, 9, 10, 12, 14, 16, 18, 20, 25, 30, 35, 40, 45, 50, 55, 60, 65, 70, 75, 80, 82, 84, 86, 88, 90, 91, 92, 93, 94, 95, 96, 97, 98, 99, 99.9, 99.99, or about 99.999%. The curable calcium phosphate composition or cured product thereof can extend into the pore space of the porous structure to any suitable depth from the surface, such as equal to, less than, or more than about 1 mm, 2, 3, 4, 5, 6, 7, 8, 9, 10, 12, 14, 16, 18, 20, 22, 24, 26, 28, 30, 32, 34, 36, 38, 40, 45, 50, 55, 60, 65, 70, 75, 80, 85, 90, 95, or about 100 mm or more. In some embodiments, the curable calcium phosphate composition can extend throughout the pore space of the porous structure.

The porous structure can include any suitable material. In various embodiments, the porous structure includes a linear olefin polymer or copolymer, an acrylonitrile butadiene styrene (ABS) polymer, an acrylic polymer, a celluloid polymer, a cellulose acetate polymer, a cyclic olegin copolymer (COC), an ethylene-vinyl acetate (EVA) polymer, an ethylene vinyl alcohol (EVOH) polymer, an ethylene n-butyl acetate polymer (EnBA), a fluoroplastic, an ionomer, an acrylic/PVC alloy, a liquid crystal polymer (LCP), a polyacetal polymer (POM or acetal), a polyacrylate polymer, a polymethylmethacrylate polymer (PMMA), a polyacrylonitrile polymer (PAN or acrylonitrile), a polyamide polymer (PA or nylon), a polyamide-imide polymer (PAI), a polyaryletherketone polymer (PAEK), a polybutadiene polymer (PBD), a polybutylene polymer (PB), a polybutylene terephthalate polymer (PBT), a polycaprolactone polymer (PCL), a polychlorotrifluoroethylene polymer (PCTFE), a polytetrafluoroethylene polymer (PTFE), a polyethylene terephthalate polymer (PET), a polycyclohexylene dimethylene terephthalate polymer (PCT), a polycarbonate polymer (PC), a polyhydroxyalkanoate polymer (PHA), a polyketone polymer (PK), a polyester polymer, a polyethylene polymer (PE), a polyetheretherketone polymer (PEEK), a polyetherketoneketone polymer (PEKK), a polyetherketone polymer (PEK), a polyetherimide polymer (PEI), a polyethersulfone polymer (PES), a polyethylenechlorinate polymer (PEC), a polyimide polymer (PI), a polylactic acid polymer (PLA), a polymethylpentene polymer (PMP), a polyphenylene oxide polymer (PPO), a polyphenylene sulfide polymer (PPS), a polyphthalamide polymer (PPA), a polypropylene polymer, a polystyrene polymer (PS), a polysulfone polymer (PSU), a polytrimethylene terephthalate polymer (PTT), a polyurethane polymer (PU), a polyvinyl acetate polymer (PVA), a polyvinyl chloride polymer (PVC), a polyvinylidene chloride polymer (PVDC), a polyamideimide polymer (PAI), a polyarylate polymer, a polyoxymethylene polymer (POM), a styrene-acrylonitrile polymer (SAN), or a combination thereof. The linear olefin polymer or copolymer can be ultra high molecular weight polyethylene (UHMWPE), high-density polyethylene (HDPE), cross-linked polyethylene (PEX or XLPE), medium density polyethylene (MDPE), linear low-density polyethylene (LLDPE), low-density polyethylene (LDPE), very structure, such as 0%, such as about 0.001 wt % to about 99 wt %, or about 0.001 wt % to about 50 wt %, or about 0.001 wt % or less, or equal to or less than about 0.01 wt %, 0.1, 1, 2, 3, 4, 5, 6, 8, 10, 12, 14, 16, 18, 20, 25, 30, 35, 40, 45, 50, 55, 60, 65, 70, 75, 80, 85, 90, 95, 96, 97, 98, 99, 99.9, 99.99 wt %, or about 99.999 wt % or more.

The one or more materials in the porous structure can include a plurality of ligaments. The plurality of ligaments can define the pores of the porous structure. The open spaces between the ligaments form a matrix of continuous channels having few or no dead ends, such that growth of soft tissue and/or bone through the porous structure is substantially uninhibited. The porous structure can be suited for contacting bone, soft tissue, or a combination thereof, and in this regard, can be useful as bone substitutes and other implants and implant components that are receptive to cell and tissue ingrowth, for example, by allowing bony tissue or other tissue to grow into the porous structure over time to enhance fixation (e.g., osseointegration) between the structure and surrounding bodily structures.

The porous structure can include or can be a prosthetic implant, such as an orthopedic implant, such as an orthopedic implant for implantation in a hip, knee, ankle, shoulder, spine, jaw, or elbow. The porous structure can include or can be a prosthetic acetabular component, a prosthetic proximal femoral component, a prosthetic distal femoral component, a prosthetic tibial component, a prosthetic humeral component, a prosthetic dental component, a prosthetic spinal component, or a combination thereof. The porous structure can include or can be an acetabular cup, a tibial cone, a glenoid implant, or a distal tibia-tallus fusion body.

In various embodiments, the present invention provides a use of the apparatus for treatment of a joint disorder or condition. For example, the present invention can provide a method including using the apparatus as an orthopedic implant. The method can include implanting the apparatus (e.g., forming the apparatus outside the body and then implanting the apparatus) or forming the apparatus in vivo (e.g., implanting the porous structure, adding the curable calcium phosphate composition or cured product thereof, and allowing the curable calcium phosphate composition to cure).

Porous Metal Structure.

The porous structure can include or can be a porous metal structure. The porous metal structure can be any suitable proportion of the porous structure, such as about 0.001 wt % to about 100 wt %, or about 50 wt % to about 100 wt %, or about 0.001 wt % or less, or less than, equal to, or greater than about 0.01 wt %, 0.1, 1, 2, 3, 4, 5, 6, 8, 10, 12, 14, 16, 18, 20, 25, 30, 35, 40, 45, 50, 55, 60, 65, 70, 75, 80, 82, 84, 86, 88, 90, 91, 92, 93, 94, 95, 96, 97, 98, 99, 99.9, 99.99, or about 99.999 wt % or more. In some embodiments, the porous structure includes a porous metal structure that is at least partially coated with or is fully encompassed by a porous non-metallic structure, wherein the porous non-metallic structure includes any one or more non-metallic materials described herein as suitable materials for the porous structure, such as PEEK. Any suitable amount of the surface area of a porous metal structure can be coated with a porous non-metallic structure in the porous structure, such as about 0.01% to about 100%, or about 80% to about 100%, or about 0.01% or less, or less than, equal to, or greater than about 0.1, 1, 2, 3, 4, 5, 6, 7, 8, 9, 10, 12, 14, 16, 18, 20, 25, 30, 35, 40, 45, 50, 55, 60, 65, 70, 75, 80, 82, 84, 86, 88, 90, 91, 92, 93, 94, 95, 96, 97, 98, 99, 99.9, or about 99.99% or more.

The porous metal structure can include any suitable metal. The metal can be a biocompatible metal. The metal can be tantalum, titanium, niobium, hafnium, tungsten, an alloy thereof (e.g., a tantalum alloy, a titanium alloy, a niobium alloy, a hafnium alloy, a tungsten alloy, a tantalum niobium alloy), or a combination thereof. The porous metal structure can include tantalum metal.

The porous metal structure can include a porous substrate including a plurality of ligaments. The plurality of ligaments can define the pores of the porous substrate and of the porous metal structure. The porous metal structure can include a biocompatible metal coating on (e.g., applied to) the plurality of ligaments of the porous substrate.

The porous substrate can have a lower density than the biocompatible metal thereon. The porous substrate can include or can be a foam having a lower density than the biocompatible metal thereon. The porous substrate can include or can be reticulated vitreous carbon foam. For example, the reticulated vitreous carbon (RVC) foam can have a plurality of vitreous carbon ligaments that define dodecahedron (12-sided) pores therebetween. RVC foam is commercially available in porosities ranging from 10 to 200 pores per cubic inch (i.e., about 0.61 to about 12 pores per cubic cm), and more specifically in porosities of 65, 80, and 100 pores per cubic inch (i.e., about 3.97, 4.88, or about 6.10 pores per cubic cm, respectively). Such RVC foam substrates may be formed by pyrolyzing an open-cell, polymer foam.

The biocompatible metal on the porous substrate can be any suitable biocompatible metal. The biocompatible metal can include a Group IV-VI refractory metal. The biocompatible metal can be tantalum, titanium, niobium, hafnium, tungsten, an alloy thereof (e.g., a tantalum alloy, a titanium alloy, a niobium alloy, a hafnium alloy, a tungsten alloy, a tantalum niobium alloy), or a combination thereof. The biocompatible metal can be tantalum. The biocompatible metal can be deposited on the porous substrate, such as via chemical vapor deposition. The biocompatible metal can cover any suitable amount of the surface area of the porous substrate (e.g., including the outer surface and the inner surfaces that form the pores), such as about 10% to about 100%, or about 90% to about 100%, or about 10% or less, or less than, equal to, or more than about 15%, 20, 25, 30, 35, 40, 45, 50, 55, 60, 65, 70, 72, 74, 76, 78, 80, 82, 84, 86, 88, 90, 91, 92, 93, 94, 95, 96, 97, 98, 99, 99.9, 99.99, or about 99.999% or more.

The porous metal structure can be suited for contacting bone, soft tissue, or a combination thereof, and in this regard, can be useful as bone substitutes and other implants and implant components that are receptive to cell and tissue ingrowth, for example, by allowing bony tissue or other tissue to grow into the porous structure over time to enhance fixation (e.g., osseointegration) between the structure and surrounding bodily structures. Such structures can provide lightweight, yet strong porous implants. Certain porous metal structures, despite having such high porosities, are capable of withstanding extreme mechanical loads at the time of implantation and over long periods of time (for example, where a highly porous, three-dimensional metallic structure is forcefully impacted and press fit into a bone, by itself or connected to another implant, and maintains its shape during impaction and following many months or years of service in the body). Such structures can be manufactured according to any suitable technique or process. An example of a porous metal structure is produced using Trabecular Metal™ Technology available from Zimmer, Inc., of Warsaw, Ind. Trabecular Metal™ is a trademark of Zimmer, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861 and in Levine, B. R., et al., "Experimental and Clinical Performance of Porous Tantalum in Orthopedic Surgery," Biomaterials 27 (2006) 4671-4681, the disclosures of which are expressly incorporated herein by reference.

In some instances, the porous metal structure can be a highly porous, three-dimensional metallic structure that is fabricated using a selective laser sintering (SLS) or other additive manufacturing-type process such as direct metal laser sintering or electron beam melting. In one example, a three-dimensional (3-D) porous article is produced in layer-wise fashion from a laser-fusible powder (e.g., a single-component metal powder), which is deposited one layer at a time. The powder is fused, remelted or sintered, by the application of laser energy that is directed to portions of the powder layer corresponding to a cross section of the article. After the fusing of the powder in each layer, an additional layer of powder is deposited, and a further fusing step is carried out, with fused portions or lateral layers fusing so as to fuse portions of previous laid layers until a three-dimensional article is complete. In certain embodiments, a laser selectively fuses powdered material by scanning cross-sections generated from a 3-D digital description of the article (e.g., from a CAD file or scan data) on the surface of a powder bed. Complex geometries can be created using such techniques, and in some instances, net shape and near net shape implants are constructed. In some embodiments, a non-porous or essentially non-porous base substrate will provide a foundation upon which a three-dimensional porous structure will be built and fused thereto using a SLS or other additive manufacturing-type process. Such substrates can incorporate one or more of a variety of biocompatible metals such as any of those disclosed herein.

Generally, the porous metal structure includes a large plurality of ligaments that define open voids (e.g., pores) or channels between the ligaments. The open spaces between the ligaments form a matrix of continuous channels having few or no dead ends, such that growth of soft tissue and/or bone through the open porous metal is substantially uninhibited. According to some aspects of the present disclosure, exterior surfaces of an open porous metal structure can feature terminating ends of the above-described ligaments. Such terminating ends can be referred to as struts, and they can generate a high coefficient of friction along an exposed porous metal surface. Such features can impart an enhanced affixation ability to an exposed porous metal surface for adhering to bone and soft tissue. Also, when such highly porous metal structures are coupled to an underlying substrate, a small percentage of the substrate may be in direct contact with the ligaments of the highly porous structure; for example, approximately 15%, 20%, or 25%, of the surface area of the substrate may be in direct contact with the ligaments of the highly porous structure.

The porous metal structure can be fabricated such that it includes a variety of densities in order to selectively tailor the structure for particular orthopedic applications (for example, by matching the structure to surrounding natural tissue in order to provide an improved matrix for tissue ingrowth and mineralization). Such structures can be isotropic or anisotropic. In this regard, according to certain embodiments, an open porous metal structure may be fabricated to have a substantially uniform porosity, density, void (pore) size, pore shape, and/or pore orientation throughout, or to have one or more features such as porosity, density, void (pore) size, pore shape, and/or pore orientation being varied within the structure, or within a portion thereof. For example, a porous metal structure may have a different pore size, pore shape, and/or porosity at different regions, layers, and surfaces of the structure. The ability to selectively tailor the structural properties of the open porous metal enables, for example, tailoring of the structure for distributing stress loads throughout the surrounding tissue and promoting tissue growth into and within the open porous metal. In some instances, a highly porous, three-dimensional metallic structure, once formed, will be infiltrated and coated with one or more coating materials such as biocompatible metals such as any of those disclosed herein.

The porous metal structure can have any suitable relative density, wherein the relative density of the porous metal structure is a percentage obtained by dividing an actual density of the porous metal structure (e.g., of the porous metal structure alone, without the curable calcium phosphate composition or cured product thereof therein) by a theoretical density of the biocompatible metal of the coating. The relative density can be about 12% to about 50%, or about 12% or less, or less than, equal to, or more than about 13%, 14, 15, 16, 17, 18, 19, 20, 22, 24, 26, 28, 30, 32, 34, 36, 38, 40, 41, 42, 43, 44, 45, 46, 47, 48, 49, or about 50% or more.

The porous metal structure can have any suitable specific compressive strength. For example, the porous metal structure (e.g., the porous metal structure alone, without the curable calcium phosphate composition or cured product thereof therein) can have a specific compressive strength of about 50 MPa to about 2,000 MPa, or about 200,000 psi, or about 100 MPa to about 500 MPa, or about 50 MPa or less, or less than, equal to, or more than about 60 MPa, 70, 80, 90, 100, 110, 120, 130, 140, 150, 160, 165 (i.e., about 24,000 psi), 170, 175, 180, 185, 190, 195, 200, 225, 250, 275, 300, 350, 400, 450, 500, 600, 700, 800, 900, 1,000, 1,250, 1,500, 1,750, 2,000, 5,000, 10,000, 20,000, 50,000, 100,000, 150,000, or about 200,000 psi or more.

Method of Forming the Apparatus.

Various embodiments of the present invention provide a method of forming the apparatus including the porous structure at least partially in contact with the curable calcium phosphate composition or a cured product thereof. The method can be any suitable method that generates an embodiment of the apparatus described herein. The method can include placing the curable calcium phosphate composition at least partially in contact with the porous structure to form the apparatus. The placing can include placing the curable calcium phosphate composition into the porous structure (e.g., into at least some of the pore space in the porous structure), around the porous structure (e.g., in contact with an external surface of the porous structure), or a combination thereof. The placing can be any suitable placing, such as injecting (e.g., from a syringe via a needle), perfusing, placing by hand or with a spatula or other surgical tool, diffusing, and the like. The method can include allowing the curable calcium phosphate composition to cure.

The method can be performed in vivo, such as including some steps in vivo (with other steps outside the body) or all steps performed in vivo. The method can include or can be a primary or revision surgery, such as of a hip implant, a leg implant, a shoulder implant, a jaw implant, a spine implant, or an ankle implant. The method can include treatment of osteolytic lesions (e.g., by implanting the curable composition, cured product thereof, porous structure, or any combination thereof, in contact therewith). The method can be a surgical method, such as wherein the curable calcium phosphate composition is placed in contact with the porous structure in vivo, or wherein the curable calcium phosphate composition is placed in contact with the porous structure outside the body and the apparatus is then implanted. The curable calcium phosphate composition can be allowed to cure before implantation or afterwards.

In various embodiments, the method can include a primary implantation surgery or revision surgery for an acetabular cup implant, as illustrated in FIG. 1. The acetabular cup 100 can include a porous structure with a porosity similar to trabecular bone on the side that contacts the pelvis 105, and a smooth surface on the side that contacts the proximal femur 120 (not shown). The acetabular cup 100 can be used with cannulated fenestrated screws 115 to anchor the cup to the pelvis 105. The curable calcium phosphate composition 110 is placed in regions that facilitate augmentation of screw fixation. The curable calcium phosphate composition 110 is placed in regions that augment fixation of the acetabular cup 100 to the acetabulum of the pelvis 105. At least some of the curable calcium phosphate composition 110 penetrates the pores of the porous structure of the acetabular cup 100. The curable calcium phosphate composition 110 can reduce or eliminate loosening of the implanted cup due to poor quality of bone in the acetabulum. The curable calcium phosphate composition 110 can create a continuous osteoconductive region between the porous structure and the acetabulum.

Figure 2A:
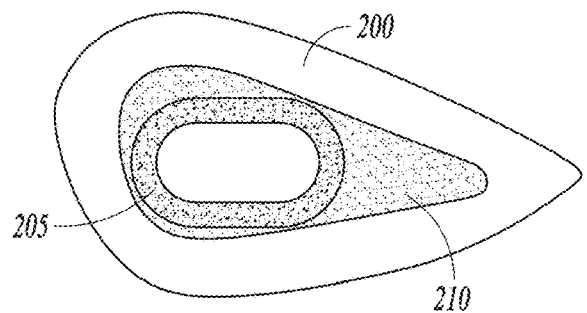
FIGS. 2A-B illustrate an implanted apparatus including a curable calcium phosphate composition and a porous structure, in accordance with various embodiments.
Figure 2B:
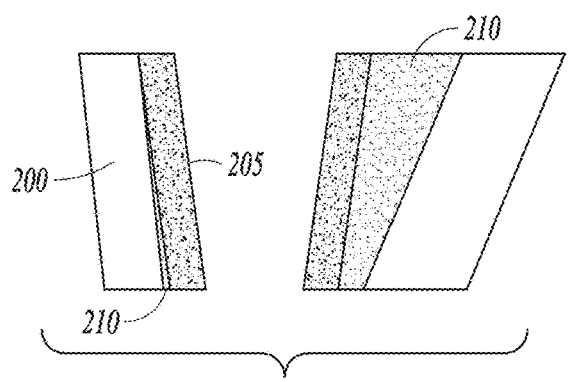

In various embodiments, the method can include a primary implantation surgery or revision surgery for a tibial cone implant, as illustrated in FIGS. 2A-B. FIG. 2A shows an end-on cutaway view of a proximal tibia 200 having a tibial cone implant 205 therein, wherein the tibial cone implant 205 is a porous structure. FIG. 2B shows a side cutaway view of the tibia 200 having the tibial cone implant 205 therein. The implant includes the curable calcium phosphate composition 210 between the porous structure 205 and the bone of the tibia 200. The tibial cone implant 205 has a porosity similar to trabecular bone. The curable calcium phosphate material at least partially penetrates the porous structure of the tibial cone implant 205. The curable calcium phosphate material 210 is placed in regions of the tibia to augment the fixation of the cone implant 205 and eliminate mismatch between the endosteal contour of the tibial metaphysis that accepts the tibial cone implant 205. The curable calcium phosphate material 210 reduces or eliminates loosening of the implanted tibial cone implant 205 due to poor quality of bone in the proximal tibia 200. The curable calcium phosphate material 210 creates a continuous osteoconductive region between the tibial cone implant 205 and the tibia 200.

Figure 3:
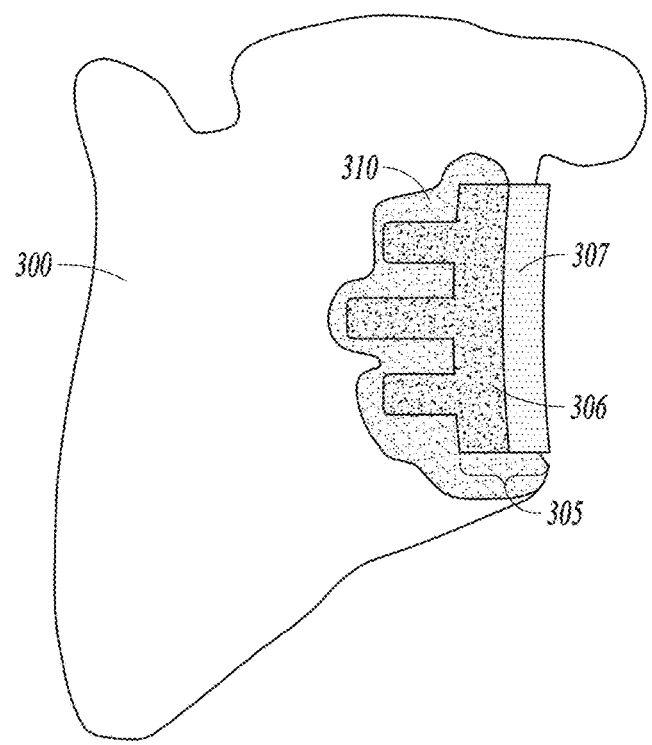
FIG. 3 illustrates an implanted apparatus including a curable calcium phosphate composition and a porous structure, in accordance with various embodiments.

In various embodiments, the method can include a primary implantation surgery or revision surgery for a glenoid implant, as illustrated in FIG. 3. The scapula 300 includes a glenoid pegged implant 305 which includes the porous structure 306 and a smooth articulating surface 307. The implant includes the curable calcium phosphate composition 310 between the porous structure 306 and the bone 300. The porous structure 306 has a porosity similar to trabecular bone. The curable calcium phosphate composition 310 provides structural fixation of the pegged components of the implant 305 within the scapula 300 to augment fixation therein. The curable calcium phosphate composition 310 at least partially penetrates into the pores of the porous structure 306. The curable calcium phosphate composition 310 improves the seating of the implant 305 by filling out small spaces between the bone 300 and the implant 305, such as may result from irregularities after reaming. The fixation of pegged glenoid implant 305 has better chances of integrating if the holes are filled with an osteoconductive material. The curable calcium phosphate material 310 is a flowable material that can be delivered with a syringe or can be a moldable material which can be inserted with pure finger pressure. The curable calcium phosphate material 310 can reduce or eliminate loosening of the implant 305 due to poor quality of bone in the scapula 300 or due to gaps between the scapula 300 and the implant 305. The curable calcium phosphate material 310 can create a continuous osteoconductive region between the implant 305 and the bone 300.

Figure 4:
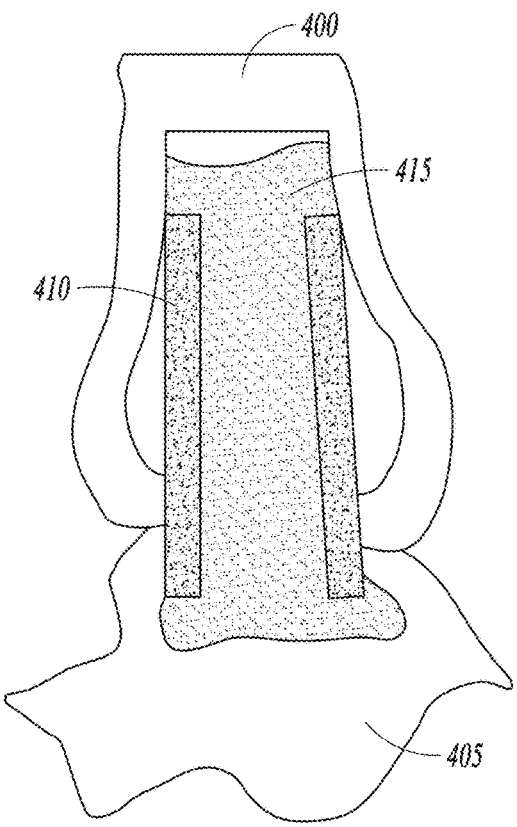
FIG. 4 illustrates an implanted apparatus including a curable calcium phosphate composition and a porous structure, in accordance with various embodiments.

In various embodiments, the method can include a primary implantation surgery or revision surgery for a total ankle replacement spacer, as illustrated in FIG. 4. The distal tibia 400 and the talus 405 include tibiotalar porous fusion implant 410, which is a porous structure having porosity similar to trabecular bone. A curable calcium phosphate composition 415 is inside the implant 410 and is between the ends of the implant 410 and the distal tibia 400 and the talus 405. The curable calcium phosphate composition 415 can be placed in the implant 410 prior to implantation or the implant 410 can be filled with the composition 415 after implantation using a port or delivery hole in the implant 410 (not shown). The curable calcium phosphate composition 415 augments the fixation of the implant 410, and eliminates mismatch between the contour of the distal tibia 400 and the implant 410, such as resulting from irregularities after reaming distal tibia 400. The curable calcium phosphate composition 415 reduces or eliminates loosening of the implant 410 due to poor quality of bone in the fusion mass. The curable calcium phosphate composition 415 creates a continuous osteoconductive region between the implant 410 and the tibia 400 and talus 405. The curable calcium phosphate composition 415 can be inductive or conductive to facilitate formation of a fusion mass (not shown).

EXAMPLES

Various embodiments of the present invention can be better understood by reference to the following Examples which are offered by way of illustration. The present invention is not limited to the Examples given herein.

Part I

Example 1-1

A low density lyophilized calcium carboxymethylcellulose is mixed in the dry state with a reactive calcium deficient (Ca:P ratio of less than 1.67) calcium phosphate (an amorphized 1:1 mixture by mass of amorphous calcium phosphate and dicalcium phosphate dihydrate), forming a mixture that is about 5.5 wt % calcium carboxymethylcellulose and about 94.5 wt % amorphous calcium phosphate. The dry powder mixture is then mixed with deionized water, forming a mixture that is 45 wt % deionized water. A flowable paste results which, upon dissociation of $Ca^{2+}$ ions, hardens into a crystalline solid. The flowable paste perfuses porous trabecular structures without phase separation of the calcium phosphate from the aqueous cellulose derivative.

Example 1-2

Sodium alginate is mixed in solution with a 1:1 by weight mixture of reactive amorphous calcium phosphate and a calcium deficient carbonate apatite (having a Ca:P molar ratio of less than 1.67 with $CO_3^{2-}$ ions occupying both A ($OH^-$ substitutions) and B ($PO_4^{3-}$ substitutions) sites in the apatite lattice), forming a mixture that has a weight ratio of sodium alginate to the mixture of reactive amorphous calcium phosphate and the calcium deficient carbonate apatite of 5.5:94.5. The mixture is lyophilized. The dry powder is then mixed with deionized water to form a mixture that is 45 wt % deionized water. A flowable paste results which, upon dissociation of $Ca^{2+}$ ions from the carbonate apatite, hardens into a crystalline solid. The flowable paste perfuses porous trabecular structures without phase separation of the calcium phosphate from the aqueous sodium alginate.

Example 1-3

Sodium carboxymethylcellulose is lyophilized with $CaCO_3$ and mixed in the dry state with a reactive calcium deficient amorphous calcium phosphate (an amorphized 1:1 mixture by mass of amorphous calcium phosphate and dicalcium phosphate dihydrate) with a sodium carboxymethylcellulose to reactive calcium deficient amorphous calcium phosphate weight ratio of 5.5:94.5. The dry powder is then mixed with autologous blood to form a mixture that is 45 wt % autologous blood. A flowable paste results which, upon dissociation of $Ca^{2+}$ and metal carbonate ions, hardens into a crystalline carbonate apatite solid. The flowable paste perfuses porous trabecular structures without phase separation of the calcium phosphate from the aqueous cellulose derivative.

Part II

This Part compares the injectability and performance of various calcium phosphate bone substitute materials (BSMs) that were injected into a porous metal Trabecular Metal™ (TMT) block (1.614 in×1.732 in). Performance characteristics included measurement of forces required to extrude the BSM into the TMT block in addition to qualitative assessment and gross histology. Mixing of BSMs was performed in PMDS (precision mixing and delivery system, P/N: 31-0001). For the purpose of this testing all materials were gamma irradiated at (25-35) KGy.

Materials. The following materials were used in this Part: Physiological saline (0.9% NaCl, VWR®); 1 cc Medallion® syringes (P/N: 30-1098); Texture Technologies TA-HD plus (Stable Micro Systems); TMT blocks (1.614 in×1.732 in); 24×14 cc PMDS (P/N: 31-0001); 4 funnels for MedMix AG (P/N: 30-1124); 6 Internal pin (P/N: 30-1125); 6×7.5 g Sample #2 powder in MedMix AG syringes (PMDS); and 6×5 cc Sample #1 powder in MedMix AG syringes (PMDS). Sample #1 was 100% $CaP_3$. Sample #2 was 91.5% $CaP_3$, 5 wt % EfferSoda® (a mixture of 10 wt % sodium carbonate and 90 wt % sodium bicarbonate), and 3.5 wt % carboxymethylcellulose. The $CaP_3$ was a 1:1 (by weight) mixture of ball-milled amorphous calcium phosphate and dicalcium phosphate dehydrate. The ball-milling was performed using a 10 mm diameter high-density $ZrO_2$ ball for 3 hours. The amorphous calcium phosphate was prepared using a low temperature double decomposition technique, by adding rapidly a calcium solution (0.36 M), to phosphate solution (0.16 M) in a basic (pH~13) media. The amorphous phase was then stabilized using three crystal growth inhibitor ions ($CO_3^{2-}$, $Mg^+$ and $P_2O_7^{4}$), freeze-dried, and heated (450° C., 1 h) to remove additional moisture and some crystal growth inhibitors. The dicalcium phosphate dehydrate also prepared using wet chemistry by adding rapidly a calcium solution (0.30 M), to phosphate solution (0.15 M) in a slightly acidic (pH~5-6) media. During precipitation, the chemical composition of the dicalcium phosphate dehydrate was controlled to approximately 10 to 25% (w/w) apatite. The dicalcium phosphate dehydrate wet cake was then vacuum dried (6 h at 37° C.), and milled to achieve a particle size of less than 125 µm.

Testing facilities. The testing facilities and the services provided by each test facility are described in Table 1.

TABLE 1

Test facilities.

| Test facility | Address | Test method |
|---|---|---|
| Isomedix | 435 Whitney Street Northborough, MA 01532 Phone#(508)393-9323 | Gamma Irradiation at 25-35 kGy |
| Zimmer Biomet Etex | 38 Sidney St. Cambridge, MA 02139 | Extrusion (Injectability) |
| Zimmer Biomet TMT | Parsippany, NJ | Sectioning and gross histology |

Figure 5A:
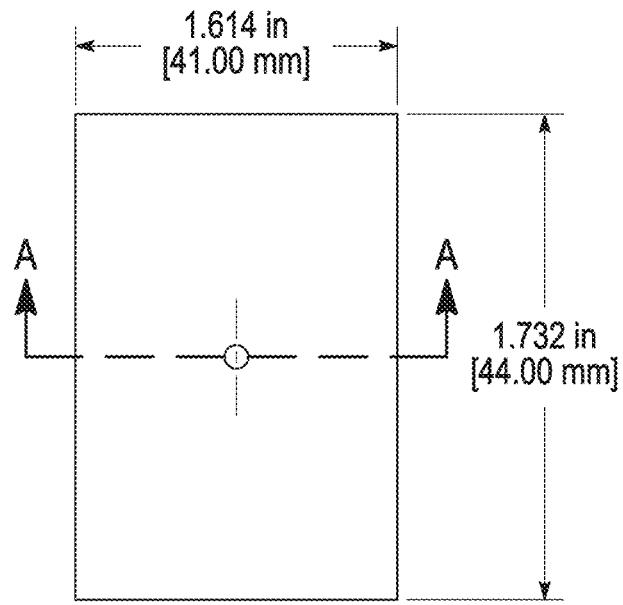
FIGS. 5A-D illustrate various views of a porous metal block, in accordance with various embodiments.
Figure 5B:
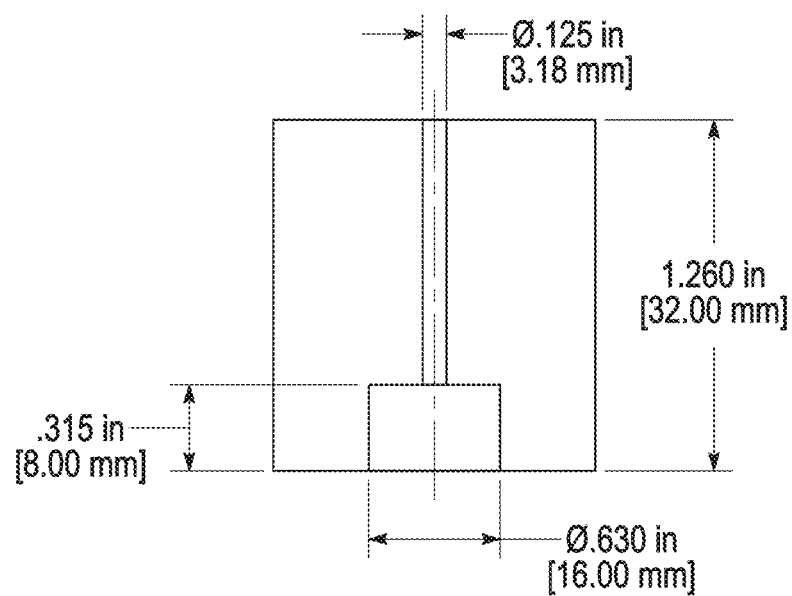
Figure 5C:
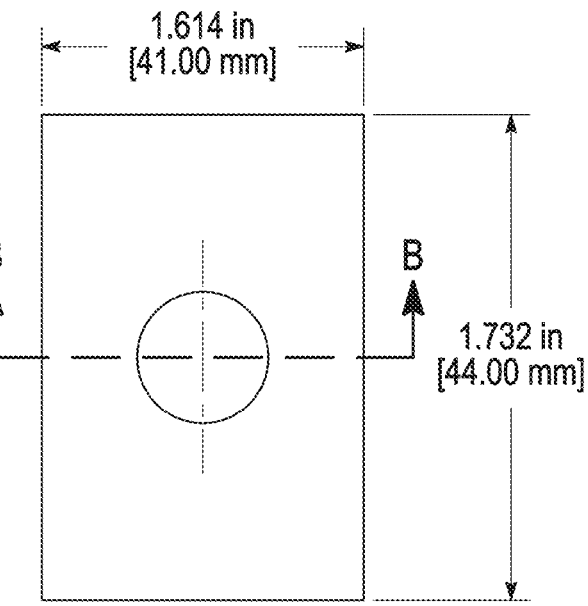
Figure 5D:
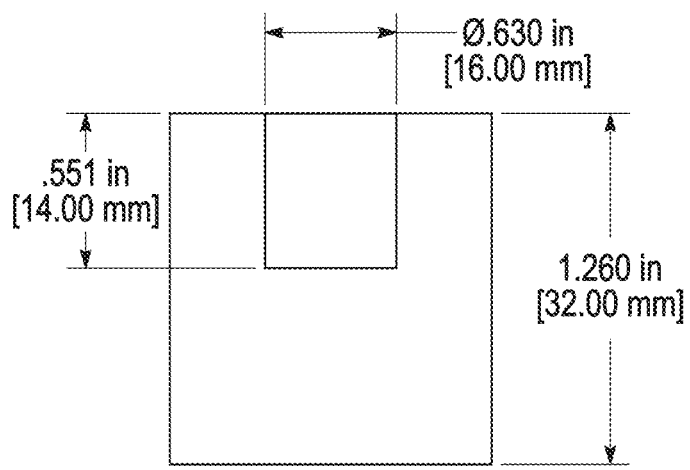

TMT blocks. FIGS. 5A-D illustrates the dimensions of the TMT block, which had a void in the middle. FIG. 5A illustrates a top view of the TMT block. FIG. 5B illustrates a cut-away view of the TMT block taken along line A-A from FIG. 5A. FIG. 5C illustrates a side view of the TMT block. FIG. 5D illustrates a cut-away view of the TMT block taken along line B-B from FIG. 5D.

Example 2-1. Testing of Samples

All testing was conducted using sterile Samples. Each ETEX product was tested according to the schedule outlined in Table 2.

TABLE 2

Testing schedule.

| Type of Cannula | Test Method | Number of Blocks | Material |
|---|---|---|---|
| 11G Cannula | Extrusion Force (Maximum and Average) | 3 | Sample #1 |
| 11G Cannula | Extrusion Force (Maximum and Average) | 4 | Sample #2 |

Figure 6:
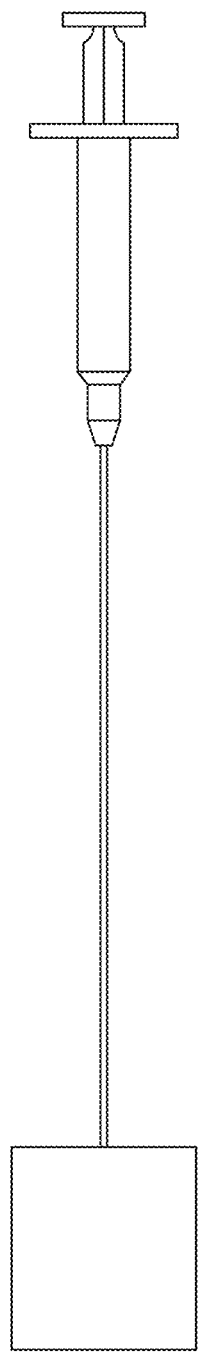
FIG. 6 illustrates an extrusion testing set up, in accordance with various embodiments.

Samples were hydrated with 0.9% sodium chloride USP saline according to the appropriate L/P ratio per each product (Sample 1=0.5 mL/g, Sample 2=0.4 mL/g) and mixed in MedMix AG syringes for approximately 60 seconds to achieve a paste with a smooth consistency. The BSM Samples were tested to measure injection force through an 8G cannula for EquivaBone and through an 11G cannula for all other products. The 1 cc Medallion® syringes (P/N: 30-1098) were attached with the 8G and 11G cannulas into the hole (0.020 in) of the TMT blocks. Each Sample paste was extruded into a TMT block from a 1 cc syringe, and the maximum filling force required to make the extrusion was measured. The extrusion testing set-up is illustrated in FIG. 6.

Example 2-2. Results

The raw data is given in Table 3. A summary of the results is given in Table 4.

Injection of Sample #1 into the TMT block showed forces higher than the accepted standard of 10 kgf. This was due to a complete fill of the simulated void and inability of the material to intrude the porous structure any further. On the contrary, the Sample #2 material consistently showed injection forces significantly lower than the accepted standard, even after the void was filled. One block was tested with 10 cc of Sample #2 and it continued to show lower injection forces in spite of the excess material injected into the block.

TABLE 3

Raw data.

| Sample | Size | 1 cc syringe # | TMT block # | L/P (mL/g) | Mean force (kg) | Maximum injection force (kg) | Comments |
|---|---|---|---|---|---|---|---|
| 1-1 | 5 cc | 1 | 1 | 0.5 | 0.071 | 0.30 | Injected through 11 G cannula |
|  |  | 2 |  |  | 0.21 | 0.72 |  |
|  |  | 3 |  |  | 0.31 | 1.60 |  |
|  |  | 4 |  |  | 0.554 | 2.71 |  |
|  |  | 5 |  |  | 3.388 | 9.83 | Hard to plunge paste by hand due to phase |
| 1-2 | 5 cc | 1 | 2 | 0.5 | 0.047 | 0.10 | Injected through 11 G cannula |
|  |  | 2 |  |  | 0.221 | 1.10 |  |
|  |  | 3 |  |  | 0.296 | 1.03 |  |
|  |  | 4 |  |  | 3.517 | 22.62 |  |
|  |  | 5 |  |  | n/a | n/a | Hard to plunge paste by hand due to phase |
| 1-3 | 5 cc | 1 | 3 | 0.5 | 0.053 | 0.42 | Injected through 11 G cannula |
|  |  | 2 |  |  | 0.072 | 0.42 |  |
|  |  | 3 |  |  | 0.198 | 0.71 |  |
|  |  | 4 |  |  | 0.366 | 1.06 |  |
|  |  | 5 |  |  | 3.309 | 12.67 | Easy to plunge |
| 2-1 | 5 cc | 1 | 4 | 0.5 | 1.62 | 2.57 | Injected through 11 G cannula |
|  |  | 2 |  |  | 2.945 | 3.76 |  |
|  |  | 3 |  |  | 2.529 | 3.36 |  |
|  |  | 4 |  |  | 3.132 | 4.01 |  |
|  |  | 5 |  |  | 2.733 | 3.61 | Easy to plunge |
| 2-2 | 5 cc | 1 | 5 | 0.4 | 1.721 | 2.92 | Injected through 11 G cannula |
|  |  | 2 |  |  | 2.695 | 3.47 |  |
|  |  | 3 |  |  | 2.774 | 3.76 |  |
|  |  | 4 |  |  | 2.702 | 3.78 |  |
|  |  | 5 |  |  | 2.688 | 3.7 |  |
|  |  | 6 |  |  | 0.706 | 3.1 | Only plunged by instrument (Texture) |
| 2-3 | 5 cc | 1 | 6 | 0.4 | 1.73 | 3.05 | Injected through 11 G cannula |
|  |  | 2 |  |  | 1.852 | 2.54 |  |
|  |  | 3 |  |  | 2.473 | 3.30 |  |
|  |  | 4 |  |  | 2.903 | 3.95 |  |
|  |  | 5 |  |  | 3.221 | 4.24 |  |
|  |  | 6 |  |  | 0.681 | 5.69 | Only plunged by instrument (Texture) |
| 2-4 | 10 cc | 1 | 7 | 0.4 | 2.481 | 4.195 | Injected through 11 G cannula. |
|  |  | 2 |  |  | 3.342 | 4.504 |  |
|  |  | 3 |  |  | 3.406 | 4.560 | On syringe #9, |
|  |  | 4 |  |  | 3.479 | 4.635 | paste was injected |
|  |  | 5 |  |  | 4.034 | 5.357 | but after 9 cc the |
|  |  | 6 |  |  | 4.409 | 5.809 | paste came out |
|  |  | 7 |  |  | 4.34 | 6.110 | from the block. |
|  |  | 8 |  |  | 4.733 | 7.513 |  |
|  |  | 9 |  |  | 3.783 | 5.485 |  |
|  |  | 10 |  |  | 6.932 | 8.846 | Only plunged by instrument (Texture) |

TABLE 4

Summary of results.

| BSM | Seq | Mean Force (kgf) | Maximum Force (kgf) | Comments |
|---|---|---|---|---|
| Sample #1 5 cc N = 3 | 1 | 0.06 ± 0.01 | 0.28 ± 0.16 |  |
|  | 2 | 0.17 ± 0.08 | 0.74 ± 0.34 |  |
|  | 3 | 0.27 ± 0.06 | 1.11 ± 0.45 |  |
|  | 4 | 1.48 ± 1.77 | 8.80 ± 12.00 | High maximum force due to complete defect fill and limited intrusion. |
|  | 5 | 3.35 ± 0.06 | 11.25 ± 2.01 | High maximum force due to complete defect fill and limited intrusion. |
| Sample #2 5 cc N = 3 | 1 | 1.67 ± 0.07 | 2.87 ± 0.27 |  |
|  | 2 | 2.46 ± 0.64 | 3.43 ± 0.35 |  |
|  | 3 | 2.39 ± 0.48 | 3.22 ± 0.62 |  |
|  | 4 | 2.77 ± 0.33 | 3.70 ± 0.37 |  |
|  | 5 | 2.77 ± 0.11 | 3.75 ± 0.17 |  |
| Sample #2 10 cc N = 1 | 1 | 2.48 | 4.20 |  |
|  | 2 | 3.34 | 4.50 |  |
|  | 3 | 3.45 | 4.56 |  |
|  | 4 | 3.48 | 4.64 |  |
|  | 5 | 4.03 | 5.36 |  |
|  | 6 | 4.41 | 5.81 |  |
|  | 7 | 4.34 | 6.11 |  |
|  | 8 | 4.73 | 7.51 |  |
|  | 9 | 3.78 | 5.49 |  |
|  | 10 | 6.93 | 8.85 |  |

Figure 7A:
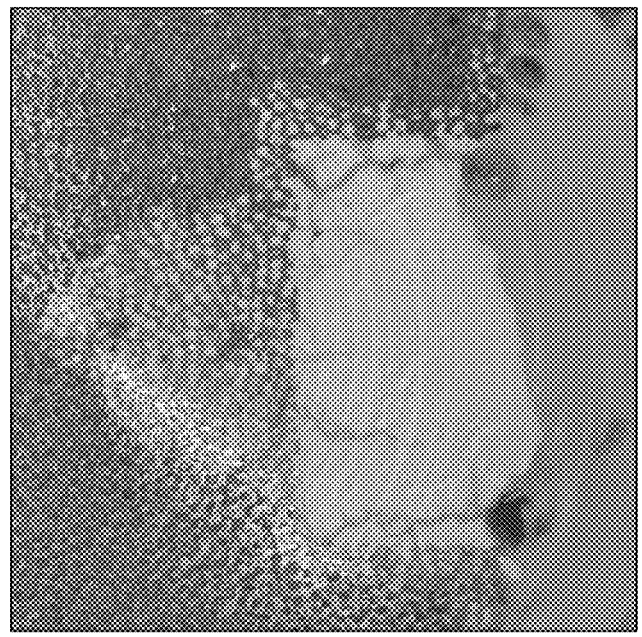
FIGS. 7A-B illustrate penetration of a bone substitute material through a porous metal block, in accordance with various embodiments.
Figure 7B:
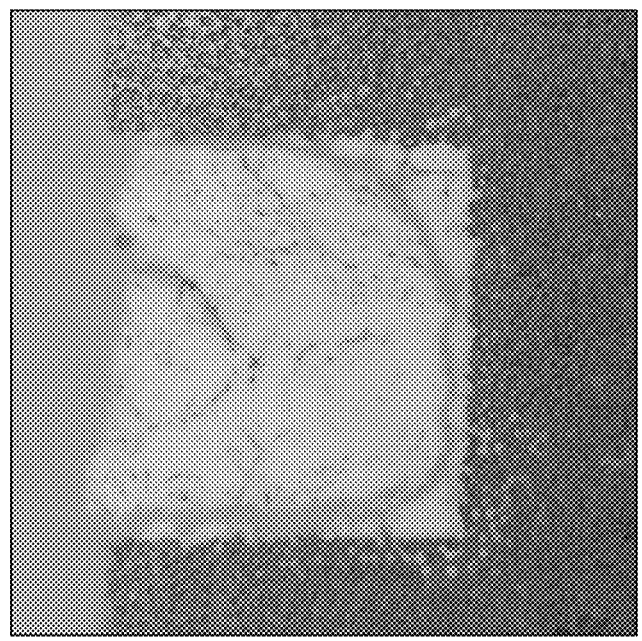

FIGS. 7A-B illustrate photographs of Sample #2 after infusion thereof through into the TMT block. The TMT block was cut in order to better show the Sample in the block. The block sections showed penetration of Sample #2 through porous TMT block. The material showed intrusion and inter-digitation with the metal surrounding the void at the center of the TMT block.

Example 2-3. Analysis

Sample #2 showed qualitative intrusion into the porous TMT block. The injection forces for Sample #2 were also below the accepted standard of 10 kgf, the approximate capability of an average human hand. In comparison, injection forces for Sample #1 were higher due to limited intrusion.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

ADDITIONAL EMBODIMENTS

The following exemplary embodiments are provided, the numbering of which is not to be construed as designating levels of importance:

Embodiment 1 provides a curable calcium phosphate composition comprising:
calcium phosphate; and
a perfusion modifier.

Embodiment 2 provides the curable calcium phosphate composition of Embodiment 1, further comprising a physiologically acceptable fluid.

Embodiment 3 provides the curable calcium phosphate composition of Embodiment 2, wherein the physiologically acceptable fluid is about 0.001 wt % to about 99.999 wt % of the composition.

Embodiment 4 provides the curable calcium phosphate composition of any one of Embodiments 2-3, wherein the physiologically acceptable fluid comprises water, saline, phosphate buffer, biological fluid, or a combination thereof.

Embodiment 5 provides the curable calcium phosphate composition of Embodiment 4, wherein the biological fluid comprises blood, a blood component, a blood product, milk, urine, saliva, seminal fluid, vaginal fluid, synovial fluid, lymph fluid, amniotic fluid, the fluid within a yolk sac of an egg, chorion of an egg, allantois of an egg, sweat, tears, or a combination thereof.

Embodiment 6 provides the curable calcium phosphate composition of any one of Embodiments 1-5, wherein the calcium phosphate is about 0.001 wt % to about 99.999 wt % of the composition.

Embodiment 7 provides the curable calcium phosphate composition of any one of Embodiments 1-6, wherein the calcium phosphate is about 40 wt % to about 70 wt % of the composition.

Embodiment 8 provides the curable calcium phosphate composition of any one of Embodiments 1-7, wherein the calcium phosphate comprises amorphous calcium phosphate, poorly crystalline calcium phosphate, hydroxyapatite, carbonated apatite, monocalcium phosphate, calcium metaphosphate, heptacalcium phosphate, dicalcium phosphate dihydrate, tetracalcium phosphate, octacalcium phosphate, calcium pyrophosphate, tricalcium phosphate, or a combination thereof.

Embodiment 9 provides the curable calcium phosphate composition of any one of Embodiments 1-8, wherein the calcium phosphate comprises amorphous calcium phosphate and a second calcium phosphate comprising poorly crystalline calcium phosphate, hydroxyapatite, carbonated apatite, monocalcium phosphate, calcium metaphosphate, heptacalcium phosphate, dicalcium phosphate dihydrate, tetracalcium phosphate, octacalcium phosphate, calcium pyrophosphate, tricalcium phosphate, or a combination thereof.

Embodiment 10 provides the curable calcium phosphate composition of any one of Embodiments 1-9, wherein the calcium phosphate comprises amorphous calcium phosphate and dicalcium phosphate dihydrate.

Embodiment 11 provides the curable calcium phosphate composition of any one of Embodiments 1-10, wherein the perfusion modifier is about 0.001 wt % to about 50 wt % of the composition.

Embodiment 12 provides the curable calcium phosphate composition of any one of Embodiments 1-11, wherein the perfusion modifier is about 0.5 wt % to about 10 wt % of the composition.

Embodiment 13 provides the curable calcium phosphate composition of any one of Embodiments 1-12, wherein the perfusion modifier is a polymer.

Embodiment 14 provides the curable calcium phosphate composition of any one of Embodiments 1-13, wherein the perfusion modifier is a polysaccharide, a nucleic acid, a carbohydrate, a protein, a polypeptide, a poly($\alpha$-hydroxy acid), a poly(lactone), a poly(amino acid), a poly(anhydride), a poly(orthoester), a poly(anhydride-co-imide), a poly(orthocarbonate), a poly($\alpha$-hydroxy alkanoate), a poly(dioxanone), a poly(phosphoester), sodium alginate, alginic acid, arabic gum, guar gum, xantham gum, gelatin, chitin, chitosan, chitosan acetate, chitosan lactate, chondroitin sulfate, N,O-carboxymethyl chitosan, a dextran, fibrin glue, glycerol, hyaluronic acid, sodium hyaluronate, a cellulose, a glucosamine, a proteoglycan, a starch, lactic acid, a poly(ethylene oxide-co-propylene oxide), sodium glycerophosphate, collagen, glycogen, a keratin, silk, poly(L-lactide) (PLLA), poly(D,L-lactide) (PDLLA), polyglycolide (PGA), poly(lactide-co-glycolide) (PLGA), poly(L-lactide-co-D, L-lactide), poly(D,L-lactide-co-trimethylene carbonate), polyhydroxybutyrate (PHB), poly($\epsilon$-caprolactone), poly($\delta$-valerolactone), poly($\gamma$-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, poly(ethylene terephthalate) polyamide, copolymers thereof, or a combination thereof.

Embodiment 15 provides the curable calcium phosphate composition of any one of Embodiments 1-14, wherein the perfusion modifier is methylcellulose, carboxymethylcellulose, hydroxypropylmethylcellulose, hydroxyethylcellulose, a salt thereof, or a combination thereof.

Embodiment 16 provides the curable calcium phosphate composition of any one of Embodiments 1-15, wherein the perfusion modifier is a lyophilized perfusion modifier.

Embodiment 17 provides the curable calcium phosphate composition of any one of Embodiments 1-16, further comprising a biologically active modifier.

Embodiment 18 provides the curable calcium phosphate composition of Embodiment 17, wherein the biologically active modifier is about 0.001 wt % to about 40 wt % of the composition.

Embodiment 19 provides the curable calcium phosphate composition of any one of Embodiments 17-18, wherein the biologically active modifier is about 0.001 wt % to about 10 wt % of the composition.

Embodiment 20 provides the curable calcium phosphate composition of any one of Embodiments 17-19, wherein the biologically active modifier is at least one of an antibody, an antibiotic, a polynucleotide, a polypeptide, a protein, an anti-cancer modifier, a growth factor, a vaccine, or a combination thereof.

Embodiment 21 provides the curable calcium phosphate composition of any one of Embodiments 1-20, further comprising a binder.

Embodiment 22 provides the curable calcium phosphate composition of Embodiment 21, wherein the binder is about 0.001 wt % to about 20 wt % of the composition.

Embodiment 23 provides the curable calcium phosphate composition of any one of Embodiments 21-22, wherein the binder is about 0.001 wt % to about 5 wt % of the composition.

Embodiment 24 provides the curable calcium phosphate composition of any one of Embodiments 21-23, wherein the binder is at least one of a) a polysaccharide, a nucleic acid, a carbohydrate, a protein, a polypeptide, a poly(α-hydroxy acids), a poly(lactone), a poly(amino acid), a poly(anhydride), a poly(orthoester), a poly(anhydride-co-imide), a poly(orthocarbonate), a poly(α-hydroxy alkanoate), a poly(dioxanone), a poly(phosphoester), poly(L-lactide) (PLLA), poly(D,L-lactide) (PDLLA), polyglycolide (PGA), poly(lactide-co-glycolide) (PLGA), poly(L-lactide-co-D, L-lactide), poly(D,L-lactide-co-trimethylene carbonate), polyhydroxybutyrate (PHB), poly(ε-caprolactone), poly(δ-valerolactone), poly(γ-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, a polyethylene, polymethylmethacrylate, a carbon fiber, poly(ethylene glycol), poly(ethylene oxide), poly(vinyl alcohol), poly(vinylpyrrolidone), poly(ethyloxazoline), a poly(ethylene oxide)-co-poly(propylene oxide) block copolymer, poly(ethylene terephthalate)polyamide, and copolymers thereof; b) a homo- or co-polymer having one or more monomers selected from the group consisting of acrolein potassium, (meth)acrylamides, (meth)acrylic acid and salts thereof, (meth)acrylates, acrylonitrile, ethylene, ethylene glycol, ethyleneimine, ethyleneoxide, styrene sulfonate, vinyl acetate, vinyl alcohol, vinyl chloride, and vinylpyrrolidone); c) a polyphenol complexing agent selected from a gallotannin, a ellagitannin, a taragallotannin, a caffetannin, a proanthocyanidin, catechin, epicatechin, chlorogenic acid, and arbutin; and d) an agent selected from alginic acid, arabic gum, guar gum, xanthan gum, gelatin, chitin, chitosan, chitosan acetate, chitosan lactate, chondroitin sulfate, N,O-carboxymethyl chitosan, a dextran, fibrin glue, glycerol, hyaluronic acid, sodium hyaluronate, a cellulose, a glucosamine, a proteoglycan, a starch, lactic acid, a poly(ethylene oxide-co-propylene oxide), sodium glycerophosphate, collagen, glycogen, a keratin, and silk.

Embodiment 25 provides the curable calcium phosphate composition of any one of Embodiments 1-24, wherein the composition further comprises an effervescent agent.

Embodiment 26 provides the curable calcium phosphate composition of Embodiment 25, wherein the effervescent agent is about 0.001 wt % to about 40 wt % of the composition.

Embodiment 27 provides the curable calcium phosphate composition of any one of Embodiments 25-26, wherein the effervescent agent comprises a combination of at least two compounds.

Embodiment 28 provides the curable calcium phosphate composition of any one of Embodiments 25-27, wherein the effervescent agent comprises a carbonate compound and a bicarbonate compound which react upon hydration of said composition to produce carbon dioxide.

Embodiment 29 provides the curable calcium phosphate composition of any one of Embodiments 1-28, wherein the composition further comprises demineralized bone.

Embodiment 30 provides the curable calcium phosphate composition of Embodiment 29, wherein the demineralized bone comprises demineralized bone fibers.

Embodiment 31 provides the curable calcium phosphate composition of any one of Embodiments 29-30, wherein the demineralized bone is about 0.001 wt % to about 40 wt % of the composition.

Embodiment 32 provides a method comprising using the composition of any one of Embodiments 1-31 or a cured product thereof for treatment of a joint disorder or condition.

Embodiment 33 provides a cured product of the curable calcium phosphate composition of any one of Embodiments 1-31.

Embodiment 34 provides an apparatus comprising a porous structure at least partially in contact with the curable calcium phosphate composition of any one of Embodiments 1-31 or a cured product thereof.

Embodiment 35 provides the apparatus of Embodiment 34, wherein the porous structure comprises a linear olefin polymer or copolymer, an acrylonitrile butadiene styrene (ABS) polymer, an acrylic polymer, a celluloid polymer, a cellulose acetate polymer, a cyclic olegin copolymer (COC), an ethylene-vinyl acetate (EVA) polymer, an ethylene vinyl alcohol (EVOH) polymer, an ethylene n-butyl acetate polymer (EnBA), a fluoroplastic, an ionomer, an acrylic/PVC alloy, a liquid crystal polymer (LCP), a polyacetal polymer (POM or acetal), a polyacrylate polymer, a polymethylmethacrylate polymer (PMMA), a polyacrylonitrile polymer (PAN or acrylonitrile), a polyamide polymer (PA or nylon), a polyamide-imide polymer (PAI), a polyaryletherketone polymer (PAEK), a polybutadiene polymer (PBD), a polybutylene polymer (PB), a polybutylene terephthalate polymer (PBT), a polycaprolactone polymer (PCL), a polychlorotrifluoroethylene polymer (PCTFE), a polytetrafluoroethylene polymer (PTFE), a polyethylene terephthalate polymer (PET), a polycyclohexylene dimethylene terephthalate polymer (PCT), a polycarbonate polymer (PC), a polyhydroxyalkanoate polymer (PHA), a polyketone polymer (PK), a polyester polymer, a polyethylene polymer (PE), a polyetheretherketone polymer (PEEK), a polyetherketoneketone polymer (PEKK), a polyetherketone polymer (PEK), a polyetherimide polymer (PEI), a polyethersulfone polymer (PES), a polyethylenechlorinate polymer (PEC), a polyimide polymer (PI), a polylactic acid polymer (PLA), a polymethylpentene polymer (PMP), a polyphenylene oxide polymer (PPO), a polyphenylene sulfide polymer (PPS), a polyphthalamide polymer (PPA), a polypropylene polymer, a polystyrene polymer (PS), a polysulfone polymer (PSU), a polytrimethylene terephthalate polymer (PTT), a polyurethane polymer (PU), a polyvinyl acetate polymer (PVA), a polyvinyl chloride polymer (PVC), a polyvinylidene chloride polymer (PVDC), a polyamideimide polymer (PAI), a polyarylate polymer, a polyoxymethylene polymer (POM), a styrene-acrylonitrile polymer (SAN), or a combination thereof. The linear olefin polymer or copolymer can be ultra high molecular weight polyethylene (UHMWPE), high-density polyethylene (HDPE), cross-linked polyethylene (PEX or XLPE), medium density polyethylene (MDPE), linear low-density polyethylene (LLDPE), low-density polyethylene (LDPE), very low-density polyethylene (VLDPE), a copolymer thereof, or a combination thereof.

Embodiment 36 provides the apparatus of any one of Embodiments 34-35, wherein the porous structure comprises a porous metal structure.

Embodiment 37 provides the apparatus of Embodiment 36, wherein the porous metal structure is about 0.001 wt % to about 100 wt % of the porous structure.

Embodiment 38 provides the apparatus of any one of Embodiments 34-37, wherein the curable calcium phosphate composition or cured product thereof is at least partially within the porous structure.

Embodiment 39 provides the apparatus of any one of Embodiments 36-38, wherein the curable calcium phosphate composition or cured product thereof is at least partially within the porous metal structure.

Embodiment 40 provides the apparatus of any one of Embodiments 36-39, wherein the porous metal structure comprises at least one of tantalum, titanium, niobium, hafnium, tungsten, an alloy thereof, or a combination thereof.

Embodiment 41 provides the apparatus of any one of Embodiments 36-40, wherein the porous metal structure comprises tantalum.

Embodiment 42 provides the apparatus of any one of Embodiments 36-41, wherein the porous metal structure comprises
- a porous substrate comprising a plurality of ligaments that define pores of the porous substrate; and
- a biocompatible metal coating on the plurality of ligaments of the porous substrate.

Embodiment 43 provides the apparatus of Embodiment 42, wherein the porous substrate comprises a foam having lower density than the biocompatible metal coating thereon.

Embodiment 44 provides the apparatus of any one of Embodiments 42-43, wherein the porous substrate comprises reticulated vitreous carbon foam.

Embodiment 45 provides the apparatus of any one of Embodiments 42-44, wherein the biocompatible metal comprises tantalum, titanium, niobium, hafnium, tungsten, an alloy thereof, or a combination thereof.

Embodiment 46 provides the apparatus of any one of Embodiments 42-45, wherein the biocompatible metal comprises tantalum.

Embodiment 47 provides the apparatus of any one of Embodiments 42-46, wherein the relative density of the porous metal structure is about 12% to about 50%, the relative density being a percentage obtained by dividing an actual density of the porous metal structure by a theoretical density of the biocompatible metal of the coating.

Embodiment 48 provides the apparatus of any one of Embodiments 36-47, wherein the specific compressive strength of the porous metal structure is at least 24,000 psi.

Embodiment 49 provides the apparatus of any one of Embodiments 34-48, wherein the porous structure comprises a prosthetic implant for implantation in a hip, knee, ankle, shoulder, spine, jaw, or elbow.

Embodiment 50 provides the apparatus of any one of Embodiments 34-49, wherein the porous structure comprises a prosthetic acetabular component, a prosthetic proximal femoral component, a prosthetic distal femoral component, a prosthetic tibial component, a prosthetic humeral component, a prosthetic dental component, a prosthetic spinal component, or a combination thereof.

Embodiment 51 provides the apparatus of any one of Embodiments 34-50, wherein the porous structure comprises an acetabular cup, a tibial cone, a glenoid implant, or a distal tibia-talus fusion body.

Embodiment 52 provides the apparatus of any one of Embodiments 36-51, wherein the porous metal structure comprises
- a porous substrate comprising a plurality of ligaments that define pores of the porous substrate, the porous substrate comprising reticulated vitreous carbon foam; and
- a biocompatible metal coating on the plurality of ligaments of the porous substrate, the biocompatible metal coating comprising tantalum metal.

Embodiment 53 provides a method comprising using the apparatus of any one of Embodiments 34-52 for treatment of a joint disorder or condition.

Embodiment 54 provides a method of forming the apparatus of any one of Embodiments 34-53, the method comprising:

placing the curable calcium phosphate composition at least partially in contact with the porous structure, to form the apparatus of any one of Embodiments 34-53.

Embodiment 55 provides the method of Embodiment 54, wherein the placing comprises placing the curable calcium phosphate composition into the porous structure, around the porous structure, or a combination thereof.

Embodiment 56 provides the method of any one of Embodiments 54-55, wherein the method is performed in vivo.

Embodiment 57 provides the method of Embodiment 56, further comprising implanting the porous structure in a subject prior to placing the curable calcium phosphate composition at least partially in contact with the porous structure.

Embodiment 58 provides the method of any one of Embodiments 54-57, wherein the placing of the curable calcium phosphate composition in contact with the porous structure is performed outside the body.

Embodiment 59 provides the method of Embodiment 58, further comprising implanting the porous structure in a subject after placing the curable calcium phosphate composition at least partially in contact with the porous structure.

Embodiment 60 provides the method of any one of Embodiments 54-59, wherein the method comprises primary or revision surgery of a hip implant, a leg implant, a shoulder implant, a spine implant, a jaw implant, or an ankle implant.

Embodiment 61 provides the method of any one of Embodiments 54-60, wherein the method comprises treatment of osteolytic lesions.

Embodiment 62 provides the composition, apparatus, or method of any one or any combination of Embodiments 1-61 optionally configured such that all elements or options recited are available to use or select from.

What is claimed is:

1. An apparatus comprising:
a porous metal structure comprising
- a porous substrate comprising a plurality of ligaments that define pores of the porous substrate, and
- a biocompatible metal coating on the plurality of ligaments of the porous substrate; and
a curable calcium phosphate composition or a cured product thereof at least partially in contact with the porous metal structure and injection-perfused into the pore space of the porous metal structure to a depth of greater than 6 mm from a surface of the porous metal structure and greater than 10 pore diameters from the surface of the porous metal structure, the curable calcium phosphate composition comprising
calcium phosphate,
a perfusion modifier, wherein the perfusion modifier is 0.5 wt % to 5 wt % of the curable calcium phosphate composition, wherein the perfusion modifier is methylcellulose, carboxymethylcellulose, hydroxypropylmethylcellulose, hydroxyethylcellulose, a salt thereof or a combination thereof, and
a physiologically acceptable fluid.

2. The apparatus of claim 1, wherein the curable calcium phosphate composition further comprises a binder.

3. The apparatus of claim 1, wherein the curable calcium phosphate composition further comprises an effervescent agent that is 1 wt % to 10 wt % of the curable calcium phosphate composition.

4. The apparatus of claim 1, wherein the curable calcium phosphate composition further comprises demineralized bone.

5. The apparatus of claim 1, wherein the porous metal structure is at least partially in contact with the curable calcium phosphate composition or the cured product of the curable calcium phosphate composition.

6. The apparatus of claim 1, wherein the porous metal structure comprises at least one of tantalum, titanium, niobium, hafnium, tungsten, an alloy thereof, or a combination thereof.

7. The apparatus of claim 1, wherein the porous substrate comprises a foam having lower density than the biocompatible metal coating thereon.

8. The apparatus of claim 1, wherein the relative density of the porous metal structure is about 12% to about 50%, the relative density being a percentage obtained by dividing an actual density of the porous metal structure by a theoretical density of the biocompatible metal of the coating.

9. The apparatus of claim 1, wherein the specific compressive strength of the porous metal structure is at least 24,000 psi.

10. The apparatus of claim 1, wherein the porous metal structure comprises
a porous substrate comprising a plurality of ligaments that define pores of the porous substrate, the porous substrate comprising reticulated vitreous carbon foam; and
a biocompatible metal coating on the plurality of ligaments of the porous substrate, the biocompatible metal coating comprising tantalum metal.

11. A method comprising treating a joint disorder or condition with the apparatus of claim 1.

12. A method of forming the apparatus of claim 1, the method comprising:
injecting by syringe the curable calcium phosphate composition into the porous metal structure to a depth of greater than 6 mm from a surface of the porous metal structure and greater than 10 pore diameters from the surface of the porous metal structure with a maximum injection force of less than 10 kgf, and optionally curing the curable calcium phosphate composition, to form the apparatus of claim 1.

13. The apparatus of claim 1, wherein the curable calcium phosphate composition or the cured product thereof is injection-perfused into the pore space of the porous metal structure to a depth of 7 mm to 100 mm from the surface of the porous metal structure.

14. An apparatus comprising:
a porous metal structure comprising
a porous substrate comprising a plurality of ligaments that define pores of the porous substrate, and
a biocompatible metal coating on the plurality of ligaments of the porous substrate; and
a curable calcium phosphate composition at least partially in contact with the porous metal structure and injection-perfused through an injection surface area of the porous metal structure into the pore space of the porous metal structure in an amount of at least 0.5 mL of the curable calcium phosphate composition per about 150 mm$^2$ of the injection surface area, wherein a maximum injection force to inject by syringe more of the curable calcium phosphate composition through the injection surface area into the pore space of the porous metal structure such that the curable calcium phosphate composition reaches a depth of greater than 6 mm from a surface of the porous metal structure and greater than 10 pore diameters from the surface of the porous metal structure is less than 10 kgf, the curable calcium phosphate composition comprising
calcium phosphate,
a perfusion modifier, wherein the perfusion modifier is 0.5 wt % to 5 wt % of the curable calcium phosphate composition, wherein the perfusion modifier is methylcellulose, carboxymethylcellulose, hydroxypropylmethylcellulose, hydroxyethylcellulose, a salt thereof or a combination thereof, and
a physiologically acceptable fluid.

15. The apparatus of claim 14, wherein the maximum injection force to inject by syringe more of the curable calcium phosphate composition through the injection surface area into the pore space of the porous metal structure is measured using a 11G cannula between the syringe and the injection surface area.

16. The apparatus of claim 14, wherein the maximum injection force to inject by syringe more of the curable calcium phosphate composition through the injection surface area into the pore space of the porous metal structure ranges from 3.1 kgf to less than 10 kgf per about 1500 mm$^2$ of the injection surface area.

17. The apparatus of claim 1, wherein the perfusion modifier is carboxymethylcellulose, a salt thereof, or a combination thereof.

* * * * *